(12) United States Patent
Martin Molina et al.

(10) Patent No.: US 9,822,379 B2
(45) Date of Patent: Nov. 21, 2017

(54) HIGHLY INDUCIBLE DUAL-PROMOTER LENTIVIRAL TET-ON SYSTEM

(75) Inventors: Francisco Martin Molina, Sevilla (ES); Karim Benabdellah El Khlanji, Sevilla (ES); Marien Cobo Pulido, Sevilla (ES); Miguel Garcia Toscano, Sevilla (ES); Pilar Munoz Fernandez, Sevilla (ES)

(73) Assignees: FUNDACIÓN PÚBLICA ANDALUZA PROGRESO Y SALUD, Seville (ES); INSTITUTO DE SALUD CARLOS III, Madrid (ES)

( * ) Notice: Subject to any disclaimer, the term of this patent is extended or adjusted under 35 U.S.C. 154(b) by 0 days.

(21) Appl. No.: 14/118,880

(22) PCT Filed: May 21, 2012

(86) PCT No.: PCT/EP2012/059408
§ 371 (c)(1),
(2), (4) Date: Dec. 20, 2013

(87) PCT Pub. No.: WO2012/156535
PCT Pub. Date: Nov. 22, 2012

(65) Prior Publication Data
US 2014/0107190 A1 Apr. 17, 2014

(30) Foreign Application Priority Data

May 19, 2011 (EP) .................................. 11166754

(51) Int. Cl.
*C12N 15/86* (2006.01)
*C07H 21/04* (2006.01)
*C12P 21/02* (2006.01)
*A61K 48/00* (2006.01)

(52) U.S. Cl.
CPC .......... *C12N 15/86* (2013.01); *A01K 2267/03* (2013.01); *A61K 48/00* (2013.01); *C12N 2740/15043* (2013.01); *C12N 2830/005* (2013.01)

(58) Field of Classification Search
None
See application file for complete search history.

(56) References Cited

FOREIGN PATENT DOCUMENTS

KR    10-2009-0020224 A    2/2009

OTHER PUBLICATIONS

Gould et al., "Endogenous GATA Factors Bind the Core Sequence of the tetO and Influence Gene Regulation with the Tetracycline System" 10(1) Molecular Therapy 127-138 (2004).*

Benabdellah, K., et al., "Development of an All-in-One Lentiviral Vector System Based on the Original TetR for the Easy Generation of Tet-ON Cell Lines", "PLoS ONE", Aug. 18, 2011, pp. 1-10, vol. 6, No. 8, e23734.
Fechner, H., et al, "A bidirectional Tet-dependent promotor construct regulating the expression of E1A for tight control of oncolytic adenovirus replication", "Journal of Biotechnology", 2007, pp. 560-574, vol. 127.
Gascon, S., et al., "Dual-promoter lentiviral vectors for constitutive and regulated gene expression in neurons", "Journal of Neuroscience Methods", 2008, pp. 104-112, vol. 168.
Gonzalez-Murillo, A., et al., "Development of Lentviral Vectors with Optimized Transcriptional Activity for the Gene Therapy of Patients with Fanconi Anemia", "Human Gene Therapy", May 2010, pp. 623-630, vol. 21.
Lee, Y., et al., "Increased utility in the CNS of a powerful neuron-specific tetracycline-regulatable adenoviral system developed using a post-transcriptional enhancer", "The Journal of Gene Medicine", Dec. 6, 2004, pp. 576-583, vol. 7.
Ogueta, S., et al., "Design and In Vitro Characterization of a Single Regulatory Module for Efficient Control of Gene Expression in Both Plasmid DNA and a Self-Inactivating Lentiviral Vector", "Molecular Medicine", Aug. 2001, pp. 569-579, vol. 7, No. 8.
Pluta, K., et al., "Tight control of transgene expression by lentivirus vectors containing second-generation tetracycline-responsive promoters", "The Journal of Gene Medicine", Jan. 17, 2005, pp. 803-817, vol. 7.
Stieger, K., et al., "In vivio gene regulation using tetracycline-regulatable systems", "Advanced Drug Delivery Reviews", Apr. 23, 2009, pp. 527-541, vol. 61.
Vaysse, L, et al., "Development of a Self-assembling Nuclear Targeting Vector System Based on the Tetracycline Repressor Protein", "The Journal of Biological Chemistry", Feb. 13, 2004, pp. 5555-5564, vol. 279, No. 7.
Wiederschain, D., et al., "Single-vector inducible lentiviral RNAi system for oncology target validation", "Cell Cycle", Feb. 2009, pp. 498-504, vol. 8, No. 3.
Curtin, JA, et al., "Bidirectional promoter interference between two widely used internal heterologous promoters in a late-generation lentiviral construct", "Gene Therapy", Jan. 24, 2008, pp. 384-390, vol. 15.
Uchida, N., et al., "The Chicken Hypersensitivity Site 4 Core Insulator Blocks Promoter Interference in Lentiviral Vectors", "Human Gene Therapy Methods", Feb. 28, 2013, pp. 117-124, vol. 24.
Dodd, I., et al., "Action at a distance in CI repressor regulation of the bacteriophage 186 genetic switch", "Molecular Microbiology", Jul. 25, 2002, pp. 679-710, vol. 45, No. 3.

(Continued)

*Primary Examiner* — Nancy J Leith
(74) *Attorney, Agent, or Firm* — Hultquist, PLLC; Steven J. Hultquist

(57) ABSTRACT

The invention relates to expression systems useful for regulated expression of a gene of interest based on the constitutive expression of the original TetR repressor and the expression of the polynucleotide driven by a constitutive promoter operably linked to an operator sequence for a tetracycline operator sequence. The system can be provided as two different polynucleotides or as an all-in-one vector. The invention also relates to vectors, host cells and viral particles according to the invention as well as to the uses thereof for in vitro and in vivo production of products of interest or for therapy.

14 Claims, 14 Drawing Sheets

(56) References Cited

OTHER PUBLICATIONS

Eszterhas, S., et al., "Transcriptional interference by independently regulated genes occurs in any relative arrangement of the genes and is influenced by chromosomal integration position", "Molecular and Cellular Biology", Jan. 2002, pp. 469-479, vol. 22, No. 2.

Gong, G., et al., "Increased Specific Labeling of INS-1 Pancreatic Beta-Cell by Using RIP-Driven Cre Mutants with Reduced Activity", "PLoS One", Jun. 5, 2015, pp. 1-16, vol. 10, No. 6.

Greger, I., et al., "Transcriptional interference perturbs the binding of Sp1 to the HIV-1 promoter", "Nucleic Acids Research", Mar. 1, 1998, pp. 1294-1300, vol. 26, No. 5.

Greger, I., et al., "Poly(A) signals control both transcriptional termination and initiation between the tandem GAL10 and GAL7 genes of *Saccharomyces cerevisiae*", "The EMBO Journal", Aug. 17, 1998, pp. 4771-4779, vol. 17, No. 16.

Hoeksema, F., et al., "Placing the RPL32 Promoter Upstream of a Second Promoter Results in a Strongly Increased Number of Stably Transfected Mammalian Cell Lines That Display High Protein Expression Levels", "Biotechnology Research International", Dec. 19, 2010, pp. 1-11 (Article ID: 492875), vol. 2011.

Prescott, E., et al., "Transcriptional collision between convergent genes in budding yeast", "PNAS", Jun. 25, 2002, pp. 8796-8801, vol. 99, No. 13.

Proudfoot, N., et al., "Transcriptional interference and termination between duplicated alpha-globin gene constructs suggests a novel mechanism for gene regulation", "Nature", Aug. 7, 1986, pp. 562-565, vol. 322.

Shearwin, K., et al., "Transcriptional interference—a crash course", "Trends Genet", Jun. 2005, pp. 339-345, vol. 21, No. 6.

Strainic, M., et al., "Promoter Interference in a Bacteriophage Lambda Control Region: Effects of a Range of Interpromoter Distances", "Journal of Bacteriology", Jan. 2000, pp. 216-220, vol. 182, No. 1.

Wang, P., et al., "Demonstration that the TyrR Protein and RNA Polymerase Complex Formed at the Divergent P3 Promoter Inhibits Binding of RNA Polymerase to the Major Promoter, P1, of the aroP Gene of *Escherichia coli*", "Journal of Bacteriology", Oct. 1998, pp. 5466-5472, vol. 180, No. 20.

\* cited by examiner

B ns of 35 U.S.C. §371 of International Patent Applica-

SEQUENCE LISTING

```
<160> NUMBER OF SEQ ID NOS: 23

<210> SEQ ID NO 1
<211> LENGTH: 61
<212> TYPE: DNA
<213> ORGANISM: Artificial Sequence
<220> FEATURE:
<223> OTHER INFORMATION: CMV minimal promoter

<400> SEQUENCE: 1
gccccgttga cgcaaatggg cggtaggcgt gtacggtggg aggtctatat aagcagagct     60
c                                                                    61

<210> SEQ ID NO 2
<211> LENGTH: 81
<212> TYPE: DNA
<213> ORGANISM: Artificial Sequence
<220> FEATURE:
<223> OTHER INFORMATION: CMV minimal promoter

<400> SEQUENCE: 2
gccccgttga cgcaaatggg cggtaggcgt gtacggtggg aggtctatat aagcagagct     60
cgtttagtga accgtcagat c                                              81

<210> SEQ ID NO 3
<211> LENGTH: 525
<212> TYPE: DNA
<213> ORGANISM: Artificial Sequence
<220> FEATURE:
<223> OTHER INFORMATION: CMV enhancer

<400> SEQUENCE: 3
```

-continued

```
gttgacattg attattgact agttattaat agtaatcaat tacggggtca ttagttcata    60
gcccatatat ggagttccgc gttacataac ttacggtaaa tggcccgcct ggctgaccgc   120
ccaacgaccc ccgcccattg acgtcaataa tgacgtatgt tcccatagta acgccaatag   180
ggactttcca ttgacgtcaa tgggtggagt atttacggta aactgcccac ttggcagtac   240
atcaagtgta tcatatgcca agtacgcccc ctattgacgt caatgacggt aaatggcccg   300
cctggcatta tgcccagtac atgaccttat gggactttcc tacttggcag tacatctacg   360
tattagtcat cgctattacc atggtgatgc ggttttggca gtacatcaat gggcgtggat   420
agcggtttga ctcacgggga tttccaagtc tccaccccat tgacgtcaat gggagtttgt   480
tttggaacca aaatcaacgg gactttccaa aatgtcgtaa caact             525
```

<210> SEQ ID NO 4
<211> LENGTH: 17
<212> TYPE: DNA
<213> ORGANISM: Artificial Sequence
<220> FEATURE:
<223> OTHER INFORMATION: tet operator sequence

<400> SEQUENCE: 4

```
ccctatcagt gatagag                                                   17
```

<210> SEQ ID NO 5
<211> LENGTH: 38
<212> TYPE: DNA
<213> ORGANISM: Artificial Sequence
<220> FEATURE:
<223> OTHER INFORMATION: tet operator sequence

<400> SEQUENCE: 5

```
ccctatcagt gatagagatc tccctatcag tgatagag                            38
```

<210> SEQ ID NO 6
<211> LENGTH: 17
<212> TYPE: DNA
<213> ORGANISM: Artificial Sequence
<220> FEATURE:
<223> OTHER INFORMATION: tet operator sequence

<400> SEQUENCE: 6

```
ccctatcagt gatagag                                                   17
```

<210> SEQ ID NO 7
<211> LENGTH: 101
<212> TYPE: DNA
<213> ORGANISM: Artificial Sequence
<220> FEATURE:
<223> OTHER INFORMATION: Transcription regulatory sequence

<400> SEQUENCE: 7

```
gccccattga cgcaaatggg cggtaggcgt gtacggtggg aggtctatat aagcagagct    60
ctccctatca gtgatagaga tctccctatc agtgatagag a                       101
```

<210> SEQ ID NO 8
<211> LENGTH: 7
<212> TYPE: PRT
<213> ORGANISM: Artificial Sequence
<220> FEATURE:
<223> OTHER INFORMATION: Nuclear localization signal- SV40 large T
      antigen

<400> SEQUENCE: 8

Pro Lys Lys Lys Arg Lys Val
1               5

<210> SEQ ID NO 9
<211> LENGTH: 16
<212> TYPE: PRT
<213> ORGANISM: Artificial Sequence
<220> FEATURE:
<223> OTHER INFORMATION: Nuclear localization signal- Nucleoplasmin

<400> SEQUENCE: 9

Lys Arg Pro Ala Ala Ile Lys Lys Ala Gly Gln Ala Lys Lys Lys Lys
1               5                   10                  15

<210> SEQ ID NO 10
<211> LENGTH: 18
<212> TYPE: PRT
<213> ORGANISM: Artificial Sequence
<220> FEATURE:
<223> OTHER INFORMATION: Nuclear localization signal- CBP80

<400> SEQUENCE: 10

Arg Arg Arg His Ser Asp Glu Asn Asp Gly Gly Gln Pro His Lys Arg
1               5                   10                  15

Arg Lys

<210> SEQ ID NO 11
<211> LENGTH: 11
<212> TYPE: PRT
<213> ORGANISM: Artificial Sequence
<220> FEATURE:
<223> OTHER INFORMATION: Nuclear localization signal- HIV-I Rev

<400> SEQUENCE: 11

Arg Gln Ala Arg Arg Asn Arg Arg Arg Trp Glu
1               5                   10

<210> SEQ ID NO 12
<211> LENGTH: 18
<212> TYPE: PRT
<213> ORGANISM: Artificial Sequence
<220> FEATURE:
<223> OTHER INFORMATION: Nuclear localization signal- HTLV-I Rex

<400> SEQUENCE: 12

Met Pro Lys Thr Arg Arg Arg Pro Arg Arg Ser Gln Arg Lys Arg Pro
1               5                   10                  15

Pro Thr

<210> SEQ ID NO 13
<211> LENGTH: 38
<212> TYPE: PRT
<213> ORGANISM: Artificial Sequence
<220> FEATURE:
<223> OTHER INFORMATION: Nuclear localization signal- hnRNP A

<400> SEQUENCE: 13

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
            35

```
<210> SEQ ID NO 14
<211> LENGTH: 9
<212> TYPE: PRT
<213> ORGANISM: Artificial Sequence
<220> FEATURE:
<223> OTHER INFORMATION: Nuclear localization signal- c-myc

<400> SEQUENCE: 14

Pro Ala Ala Lys Arg Val Lys Leu Asp
1               5

<210> SEQ ID NO 15
<211> LENGTH: 43
<212> TYPE: PRT
<213> ORGANISM: Artificial Sequence
<220> FEATURE:
<223> OTHER INFORMATION: Nuclear localization signal- rpL23a

<400> SEQUENCE: 15

Val His Ser His Lys Lys Lys Lys Ile Arg Thr Ser Pro Thr Phe Thr
1               5                   10                  15

Thr Pro Lys Thr Leu Arg Leu Arg Arg Gln Pro Lys Tyr Pro Arg Lys
            20                  25                  30

Ser Ala Pro Arg Arg Asn Lys Leu Asp His Tyr
        35                  40

<210> SEQ ID NO 16
<211> LENGTH: 4
<212> TYPE: PRT
<213> ORGANISM: Artificial Sequence
<220> FEATURE:
<223> OTHER INFORMATION: Nuclear localization signal
<220> FEATURE:
<221> NAME/KEY: VARIANT
<222> LOCATION: (2)..(2)
<223> OTHER INFORMATION: /replace="K or R"
<220> FEATURE:
<221> NAME/KEY: UNSURE
<222> LOCATION: (3)..(3)
<220> FEATURE:
<221> NAME/KEY: VARIANT
<222> LOCATION: (4)..(4)
<223> OTHER INFORMATION: /replace="K or R"

<400> SEQUENCE: 16

Lys Xaa Xaa Xaa
1

<210> SEQ ID NO 17
<211> LENGTH: 4
<212> TYPE: PRT
<213> ORGANISM: Artificial Sequence
<220> FEATURE:
<223> OTHER INFORMATION: Nuclear localization signal
<220> FEATURE:
<221> NAME/KEY: UNSURE
<222> LOCATION: (3)..(3)

<400> SEQUENCE: 17

Lys Arg Xaa Arg
1

<210> SEQ ID NO 18
<211> LENGTH: 26
<212> TYPE: DNA
<213> ORGANISM: Artificial Sequence
<220> FEATURE:
<223> OTHER INFORMATION: BamH1-tetR forward primer
```

```
<400> SEQUENCE: 18
ggatccatgt ctagattaga taaaag                                           26

<210> SEQ ID NO 19
<211> LENGTH: 31
<212> TYPE: DNA
<213> ORGANISM: Artificial Sequence
<220> FEATURE:
<223> OTHER INFORMATION: Not-tetR reverse primer

<400> SEQUENCE: 19
gcggccgctt aataagatct gaattcccgg g                                     31

<210> SEQ ID NO 20
<211> LENGTH: 30
<212> TYPE: DNA
<213> ORGANISM: Artificial Sequence
<220> FEATURE:
<223> OTHER INFORMATION: EcoR1 forward primer

<400> SEQUENCE: 20
ccggaattcg ttgacattga ttattgacta                                       30

<210> SEQ ID NO 21
<211> LENGTH: 27
<212> TYPE: DNA
<213> ORGANISM: Artificial Sequence
<220> FEATURE:
<223> OTHER INFORMATION: BamH1 reverse primer

<400> SEQUENCE: 21
cgcggatccc ggaagatgga tcggtcc                                          27

<210> SEQ ID NO 22
<211> LENGTH: 20
<212> TYPE: DNA
<213> ORGANISM: Artificial Sequence
<220> FEATURE:
<223> OTHER INFORMATION: WPRE forwdard primer

<400> SEQUENCE: 22
caccacctgt cagctccttt                                                  20

<210> SEQ ID NO 23
<211> LENGTH: 20
<212> TYPE: DNA
<213> ORGANISM: Artificial Sequence
<220> FEATURE:
<223> OTHER INFORMATION: WPRE reverse primer

<400> SEQUENCE: 23
acaacaccac ggaattgtca                                                  20
```

HIGHLY INDUCIBLE DUAL-PROMOTER LENTIVIRAL TET-ON SYSTEM

CROSS-REFERENCE TO RELATED APPLICATIONS

This application is a U.S. national phase under the provisions of 35 U.S.C. §371 of International Patent Application No. PCT/EP12/59408 filed May 21, 2012, which in turn claims priority of European Patent Application No. 11166754.9 filed May 19, 2011. The disclosures of such international patent application and European priority patent application are hereby incorporated herein by reference in their respective entireties, for all purposes.

FIELD OF THE INVENTION

The invention relates to the field of gene expression and, more in particular, to reagents and methods which allow regulated expression of a gene of interest in a cell without the requirements of cell cloning and/or antibiotic selection.

BACKGROUND OF THE INVENTION

Inducible gene expression systems based on antibiotics or hormones are a potent research tools and are constantly developed for their use in basic research and/or clinical application. Among the existing inducible transcriptional gene regulatory systems, the rtTA-regulatable system is the most widely exploited tool for controlling gene expression. This system, described for the first time in WO9429442, is based on a chimeric transcription factor consisting on the fusion of the bacterial tet repressor (TetR) with the activating domain of the viral protein 16 (VP-16), resulting in a tetracycline responsive transactivator (tTA). Random mutagenesis of tTA resulted in the rtTA (reverse tetracycline controlled trans-activator) protein that, contrary to tTA, requires the tetracycline to bind the tetO. The rtTA-based system requires the addition of tetracycline to activate transcription (TET-ON system) by allowing the binding of the rtTA to the TetO-CMV promoter. Several improvement of the rtTA have been done that improve inducibility and reduce background. However, all these tetracycline-inducible systems require a tetracycline-dependant-transactivator to activate the regulated promoter. The requirement of a transactivator for transcriptional activity has several undesired consequences, in particular, the promoter endogenous expression pattern may be altered due to the activation of the promoters of the regulated promoters, the possible activation of cellular genes due to the binding of the transactivator to pseudo-TetO sites and the toxicity caused by the presence of a transactivating domain makes these proteins very toxic. In fact, several studies have demonstrated that the rtTA-based systems can give rise to data misinterpretation due to the toxicity of the transactivator.

A doxycycline-regulated system based on the original TetR repressor was developed in 1998, by Yao and colleagues (Hum Gene Ther 1998; 9: 1939-50). The original tetR do not contain any transactivation domain and rely on blocking the activity of endogenous promoters. These characteristics should allow the design of a less-toxic Tet-inducible expression cassette that maintain the endogenous characteristics of the regulated-promoters and do not trans-activate other cellular genes. Good results have been obtained using different vector systems for gene delivery (Nghiem P. et al., Proc Natl Acad Sci USA 2001; 98: 9092-7; Trapani J G and Korn S J., BMC Neurosci 2003; 4: 15; Reeves P J. et al., Proc. Natl. Acad. Sci. USA 2002; 99: 13419-24; van de Wetering M. et al., EMBO Rep 2003; 4: 609-15 and Wiederschain D. et al. Cell Cycle 2009; 8: 498-504). However, most of these systems are based on two vector system and are reproducible only if the doxycycline-responsive cells are selected either by cloning or antibiotic selection. One of the reasons for this requirement is the high concentrations of TetR required to block promoter activity.

In spite of the potential advantages of the TetR system over the transactivator counterparts, the development of all-in-one regulatable vector systems based on TetR repressor has not been explored in detail. Wiederschain D et al. (Cell Cycle, 2009, 8: 498-504) have described a all-in-one vectors based on herpesvirus simplex (HSV). The use of HSV based vectors has been focused on neural cells due to their tropism, their toxicity and the difficulties to obtain high titre vectors.

Ogueta et al. have described an autoregulatable lentiviral vector without the requirement of antibiotic selection (Mol Med 2001; 7: 569-79). This autoregulatable vector express the TetR repressor through an internal ribosomal entry site (IRES) located downstream of the CMVTetO2 promoter. However, this systems has several potential drawbacks that could limit the use of the vector: 1—The TetR repressor and the regulated transgen are expressed through the CMVTetO promoter. Therefore, the steady-state TetR concentration required to block CMV expression will always allow expression of the transgene. 2—The efficiency of the IRES (from the EMCV) is cell-type specific and this can lead to the lost of doxycycline regulation in important target cells.

Accordingly, there is a need in the art for regulatable gene transfer vectors which overcome the disadvantages of the vectors known in the prior art.

SUMMARY OF THE INVENTION

In a first aspect, the invention relates to a polynucleotide comprising
  (i) a transcriptional regulatory sequence comprising a first promoter and at least one binding site for a transcriptional repressor wherein said first promoter and said binding site for a transcriptional repressor are arranged so that the binding of the transcriptional repressor to said binding site inhibits the transcriptional activity of the promoter and
  (ii) an expression cassette comprising a polynucleotide encoding a regulatable transcriptional repressor under the operative control of a second promoter wherein said regulatable transcriptional repressor is capable of specifically binding to the binding site in the transcriptional regulatory sequence in the absence but not in the presence of a ligand thereof.

In further aspects, the invention relates to an expression vector comprising a polynucleotide according to the invention and to a lentiviral particle or host cell comprising a vector of the invention.

In another aspect, the invention relates to a composition or kit-of-parts comprising
  (i) a first polynucleotide comprising transcriptional regulatory sequence comprising a first promoter and at least one binding site for a transcriptional repressor wherein said first promoter and said binding site are arranged so that the binding of the transcriptional repressor to said binding site inhibits the transcriptional activity of the promoter and
  (ii) a second polynucleotide comprising an expression cassette comprising a polynucleotide encoding a regulatable transcriptional repressor under the operative control of a second promoter wherein said regulatable transcriptional repressor is capable of specifically binding to the binding site in the transcriptional regulatory sequence in the absence but not in the presence of a ligand thereof.

In another aspect, the invention relates to a method for regulating the expression of a nucleic acid sequence of interest comprising the steps of
  (i) providing a host cell selected from the group consisting of:
    (a) a host cell comprising a polynucleotide according to any of claims 1 to 9 wherein the nucleic acid of interest is operatively linked to the first promoter in said polynucleotide and
    (b) a host cell comprising the first and second polynucleotides of the composition or kit-of-parts according to any of claims 14 to 20 wherein the nucleic acid is operatively linked to the first promoter of the first polynucleotide
  and
  (ii) contacting said host cell which with a ligand for the transcriptional repressor wherein said ligand is capable of binding to the transcriptional repressor producing an inactive repressor which is released from its binding site in the transcriptional regulatory sequence thereby allowing the transcription of the nucleic acid driven by the first promoter.

In an additional aspect, the invention relates to a polynucleotide, a vector, a host cell, a lentiviral particle or a composition or kit-of-parts according to the invention for use in medicine. In additional aspect, the invention relates to a polynucleotide, a vector, a host cell, a lentiviral particle or a composition or kit-of-parts according to the invention for use in the treatment of a disease which requires the expression of the polynucleotide under operative control of the transcriptional regulatory sequence.

DETAILED DESCRIPTION OF THE INVENTION

Polynucleotide of the Invention

Figure 1:
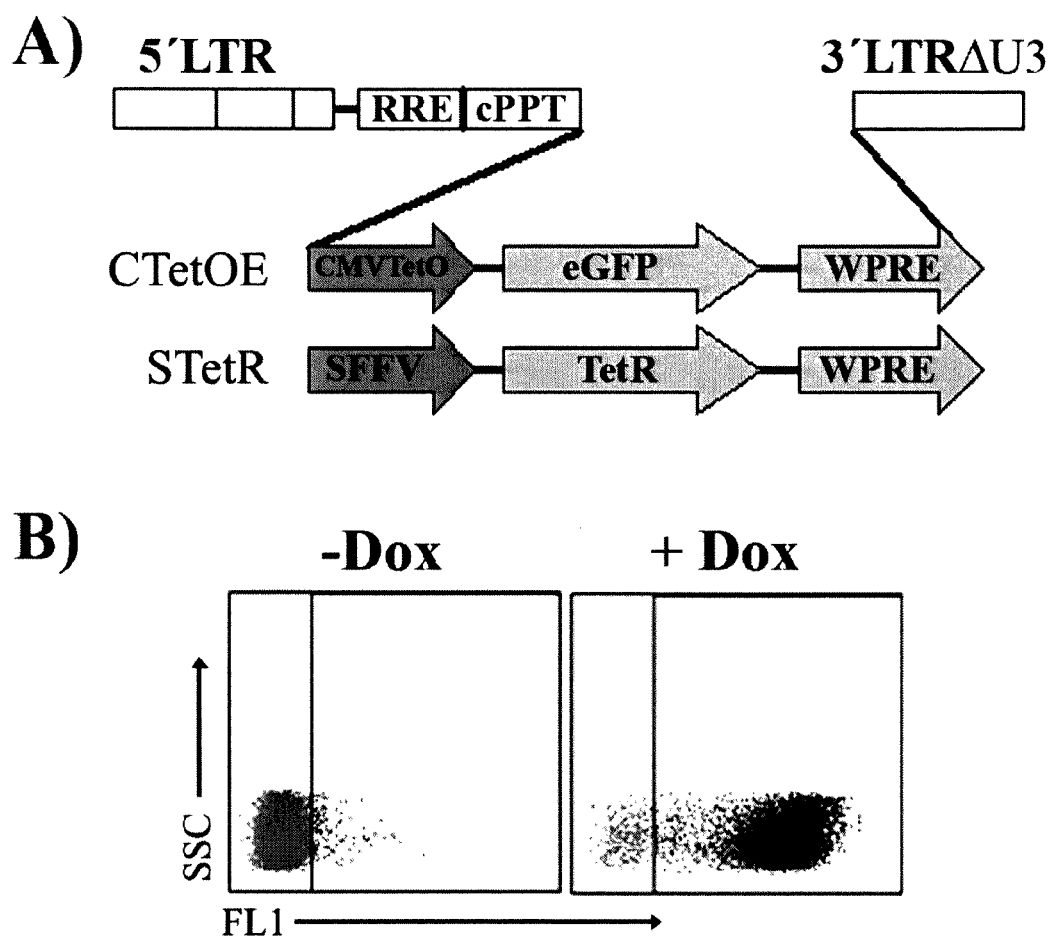
FIG. 1. Two vector system for efficient doxycycline regulation of transgenes using the TetR repressor. A) Maps of the two lentiviral vectors required for doxycycline-dependant transgene regulation. The TetR repressor is expressed through the constitutive SFFV promoter, highly active in most cell types, including hematopoietic cells. The second lentiviral vector contain the doxycycline-responsive CMV-TetO promoter (Yao et al 1998, Hum Gene Ther. 9: 1939-50) driving the expression of eGFP. B) Generation of highly inducible 293T cells after STetR and CTetOE transduction. The addition of 100 ng/ml of doxycicline was enough to achieve optimal expression of eGFP.

The authors of the present invention have developed a TetR-based all-in-one lentiviral system that efficiently generate doxycycline-responsive cell lines without the requirements of cloning and/or antibiotic selection. This vector (CEST vector) efficiently generates immortalized and primary human doxycycline-responsive cell lines. The CEST vector produce over 10,000,000 tu/ml and one single transduction on 293T cells were able to generate highly-responsive cells. This responsiveness was stable (maintained over a period of 8-10 passages) but required a minimum of 2 copies of the vector to achieved good regulation. Thus, in a first aspect, the invention relates to a polynucleotide comprising (i) a transcriptional regulatory sequence comprising a first promoter (CMV) and at least one binding site for a transcriptional repressor, wherein said first promoter and said binding sites for a transcriptional repressor are arranged so that the binding of the transcriptional repressor to said binding site inhibits the transcriptional activity of the promoter and (ii) an expression cassette comprising a polynucleotide encoding a regulatable transcriptional repressor under the operative control of a second promoter, wherein said regulatable transcriptional repressor protein is capable of specifically binding to the binding site in the transcriptional regulatory sequence in the absence but not in the presence of an inducer molecule wherein said first and said second promoters are different promoters.

As used herein, the terms "polynucleotide" or "nucleic acid molecule" are intended to include DNA molecules {e.g., cDNA or genomic DNA) and RNA molecules {e.g., mRNA) and analogs of the DNA or RNA generated using nucleotide analogs. The nucleic acid molecule may be single-stranded or double-stranded, but preferably is double-stranded DNA. The nucleic acid may be synthesized using oligonucleotide analogs or derivatives {e.g., inosine or phosphorothioate nucleotides). Such oligonucleotides may be used, for example, to prepare nucleic acids that have altered base-pairing abilities or increased resistance to nucleases.

Transcriptional Regulatory Sequence

The first component of the all-in-one vector according to the invention is a transcriptional regulatory sequence. The term "transcriptional regulatory sequence", as used herein, refers to a nucleic acid sequence which is capable of governing the expression of another nucleic acid sequence operatively linked thereto, such as a gene of interest. The transcription control sequence, preferably, is a DNA sequence. The transcriptional control sequence comprises a first promoter and at least one binding site for a transcriptional repressor wherein said first promoter and said binding site for a transcriptional repressor are arranged so that the binding of the transcriptional repressor to said binding site inhibits the transcriptional activity of the promoter.

The term "promoter", as used herein, refers to a DNA sequence that determines the site of transcription initiation for an RNA polymerase. Promoter sequences comprise motifs which are recognized and bound by polypeptides, i.e. transcription factors. The said transcription factors shall upon binding recruit RNA polymerases II, preferably, RNA polymerase I, II or III, more preferably, RNA polymerase II or III, and most preferably, RNA polymerase II. Thereby will be initiated the expression of a nucleic acid operatively linked to the transcription control sequence. It is to be understood that dependent on the type of nucleic acid to be expressed, expression as meant herein may comprise transcription of DNA sequences into RNA polynucleotides (as suitable for, e.g., anti-sense approaches, RNAi approaches or ribozyme approaches) or may comprise transcription of DNA sequences into RNA polynucleotides followed by translation of the said RNA polynucleotides into polypeptides (as suitable for, e.g., gene expression and recombinant polypeptide production approaches). In order to govern expression of a nucleic acid sequence, the transcription control sequence may be located immediately adjacent to the nucleic acid to be expressed, i.e. physically linked to the said nucleic acid at its 5' end. Alternatively, it may be located in physical proximity. In the latter case, however, the sequence must be located so as to allow functional interaction with the nucleic acid to be expressed.

Suitable promoters for use as first promoters include any promoter known in the art. In a preferred embodiment, the first promoter is a promoter functional in mammalian cells. High-level constitutive promoters are preferred for use in the vectors according to the present invention. Examples of such promoters include, without limitation, the retroviral Rous sarcoma virus (RSN) LTR promoter (optionally with the RSV enhancer), the cytomegalovirus (CMV) promoter (optionally with the CMV enhancer) [see, e.g., Boshart et al, Cell, 41:521-530 (1985)], the SN40 promoter, the dihydrofolate reductase promoter, the beta-actin promoter, the beta-active promoter linked to the enhancer derived from the cytomegalovirus (CMN) immediate early (IE) promoter, the phosphoglycerol kinase (PGK) promoter, and the EF1a promoter [Invitrogen]. Inducible promoters are regulated by exogenously supplied compounds, including, the zinc-inducible sheep metallothionine (MT) promoter, the dexamethasone (Dex)-inducible mouse mammary tumor virus (MMTV) promoter, the T7 polymerase promoter system [WO 98/10088]; the ecdysone insect promoter [No et al, Proc. Natl. Acad. Sci. USA, 93:3346-3351 (1996)], the tetracycline-repressible system [Gossen et al, Proc. Natl. Acad. Sci. USA, 89:5547-5551 (1992)], the tetracycline-inducible system [Gossen et al, Science, 268:1766-1769 (1995); see also Harvey et al, Curr. Opin. Chem. Biol, 2:512-518 (1998)], the RU486-inducible system [Wang et al, Nat. Biotech., 15:239-243 (1997) and Wang et al, Gene Ther., 4:432-441 (1997)] and the rapamycin-inducible system [Magari et al, J Clin. Invest., 100:2865-2872 (1997)]. Other types of inducible promoters which may be useful in this invention are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the gene should mimic the native expression. The native promoter may be used when expression of the gene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression. In another embodiment, the transgene product or other desirable product to be expressed is operably linked to a tissue-specific promoter. For instance, if expression in skeletal muscle is desired, a promoter active in muscle should be used. These include the promoters from genes encoding skeletal α-actin, myosin light chain 2A, dystrophin, muscle creatine kinase, as well as synthetic muscle promoters with activities higher than naturally-occurring promoters [see Li et al., Nat. Biotech, 17:241-245 (1999)]. Examples of promoters that are tissue-specific are known for liver [albumin, Miyatake et al. J Virol, 71:5124-32 (1997); hepatitis B virus core promoter, Sandig et al, Gene Ther., 3:1002-9 (1996); and alpha-fetoprotein (AFP), Arbuthnot et al, Hum. Gene Ther, 7:1503-14 (1996)], bone [osteocalcin, Stein et al, Mol. Biol. Rep., 24:185-96 (1997); and bone sialoprotein, Chen et al, J Bone Miner. Res., 11:654-64 (1996)], lymphocytes [CD2, Hansal et al., J Immunol, 161:1063-8 (1998); immunoglobulin heavy chain; T cell receptor a chain], neuronal [neuron-specific enolase (NSE) promoter, Andersen et al. Cell. Mol. Neurobiol, 13:503-15 (1993); neurofilament light-chain gene, Piccioli et al., 1991, Proc. Natl. Acad. Sci. USA, 88:5611-5 (1991); and the neuron-specific vgf gene, Piccioli et al, Neuron 15:373-84 (1995)]; among others.

Preferably, a promoter referred to herein can be derived from the Cytomegalovirus (CMV) minimal promoter and, more preferably, from human CMV (hCMV) such as the hCMV immediate early promoter derived minimal promoter as described in, e.g., Gossen and Bujard (Proc. Natl. Acad. Sci. USA, 1992, 89: 5547-5551). Modified promoters also may be used, including insertion and deletion mutation of native promoters and combinations or permutations thereof. One example of a modified promoter is the "minimal CMV promoter" as described by Gossen and Bujard (Proc. Natl. Acad. Sci. USA, 1992, 89: 5547-5551). In any case, any promoter can be tested readily for its effectiveness in the tetracycline-responsive expression system described herein by substitution for the minimal CMV promoter described herein. In a preferred embodiment, the CMV minimal promoter comprises the sequence (SEQ ID NO:1):

```
  1 GCCCCGTTGA CGCAAATGGG CGGTAGGCGT GTACGGTGGG AGGTCTATAT

51 AAGCAGAGCT C
```

In another embodiment, the CMV promoter comprises the sequence (SEQ ID NO:2):

```
  1 GCCCCGTTGA CGCAAATGGG CGGTAGGCGT GTACGGTGGG AGGTCTATAT

51 AAGCAGAGCT CGTTTAGTGA ACCGTCAGAT C
```

Additionally, the transcriptional regulatory region present in the polynucleotide of the invention may further comprise additional sequences that help to regulate the activity of the promoter, such as enhancer sequences Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 base pairs in length, and they function in cis. Enhancers usually function to increase transcription from nearby promoters. Enhancers can also contain response elements that mediate the regulation of transcription. While many enhancer sequences are known from mammalian genes (globin, elastase, albumin, fetoprotein, and insulin), typically one will use an enhancer from a eukaryotic cell virus for general expression. Preferred examples are the CMV enhancer, the SV40 enhancer, the polyoma enhancer and adenovirus enhancers. In a preferred embodiment, the polynucleotides of the invention comprise the CMV enhancer having the sequence (SEQ ID NO:3).

in SEQ ID NO: 1 having a nucleic acid sequence which is at least 70 percent, at least 80 percent, at least 90 percent, at least 95 percent, at least 97, at least 98 percent or at least 99 percent identical to the sequence as shown in SEQ ID NO: 1 or 2 or variants which hybridize thereto, preferably, under stringent hybridization conditions, are also contemplated by the present invention provided that the variants retain the properties of a minimal promoter as set forth above.

The term "binding site for a transcriptional repressor" refers to a sequence which is capable of specifically binding to a transcriptional repressor. In a preferred embodiment, the binding site for a transcriptional repressor is a tet operator sequence motif. The term "tet operator sequence motif, "tet operator", or "tetO" as used herein is intended to encompass all classes of tet operator sequences. Preferably, it relates to tetO(A), tetO (B), tetO (C), tetO (D), tetO (E), tetO (G), tetO (H), tetO(J) and tetO (Z). The nucleotide sequences of Tet repressors of members of the A, B, C, D, E, G, H, J and Z classes, and their corresponding tet operator sequences are well known in the art, see, for example, Waters 1983, Nucl. Acids Res 11:6089-6105, Hillen 1983, Nucl. Acids Res. 11:525-539, Postle 1984, Nucl. Acids Res. 12:4849-4863, Unger 1984, Gene 31: 103-108, Unger 1984, Nucl Acids Res. 12:7693-7703 and Tovar 1988, Mol. Gen. Genet. 215:76-80, which are incorporated herewith by reference with respect to the specifically disclosed tet operator sequences and in their entireties. Tet operator sequences are also disclosed in U.S. Pat. No. 5,464,758.

Thus, the transcriptional regulatory sequence for use in the vector of the invention contains sufficient tet operator sequences to bind to the tetR sequences described below. In one embodiment, the tetO sequences include at least one copy of the O-1 and O-2 sequences of the tetO. In a preferred embodiment, the tet operator sequence comprises at least

```
  1 GTTGACATTG ATTATTGACT AGTTATTAAT AGTAATCAAT TACGGGGTCA TTAGTTCATA

61 GCCCATATAT GGAGTTCCGC GTTACATAAC TTACGGTAAA TGGCCCGCCT GGCTGACCGC

121 CCAACGACCC CCGCCCATTG ACGTCAATAA TGACGTATGT TCCCATAGTA ACGCCAATAG

181 GGACTTTCCA TTGACGTCAA TGGGTGGAGT ATTTACGGTA AACTGCCCAC TTGGCAGTAC

241 ATCAAGTGTA TCATATGCCA AGTACGCCCC CTATTGACGT CAATGACGGT AAATGGCCCG

301 CCTGGCATTA TGCCCAGTAC ATGACCTTAT GGGACTTTCC TACTTGGCAG TACATCTACG

361 TATTAGTCAT CGCTATTACC ATGGTGATGC GGTTTTGGCA GTACATCAAT GGGCGTGGAT

421 AGCGGTTTGA CTCACGGGGA TTTCCAAGTC TCCACCCCAT TGACGTCAAT GGGAGTTTGT

481 TTTGGAACCA AAATCAACGG GACTTTCCAA AATGTCGTAA CAACT
```

Accordingly, a preferred minimal promoter to be used for a transcription control sequence in accordance with the present invention has a nucleic acid sequence as shown in SEQ ID NO: 1 or SEQ ID NO:2. It will, of course, be understood that variants of the said minimal promoter shown one copy of the 19 bp inverted repeat sequence of operator O2 (upper strand: 5'-CCCTATCAGTGATAGAG-3') (SEQ ID NO:4). In another embodiment, the vector contains multiple copies of these sequences in tandem arrangement, e.g., one copy of the O-1 or O-2 sequence, followed by another copy of the O-1 or O-2 sequence. In a preferred embodiment, the tet operator sequence comprises at least two copies of the 19 bp inverted repeat sequence of operator O2 (upper strand: 5'-CCCTATCAGTGATAGA GATCTC-CCTATC AGTGATAGAG-3') (SEQ ID NO:5). In another embodiment, the vector contains at least three, at least four, at least five, at least six, at least seven, at least eight, at least nine, at least 10 or more tandem copies of the O-1 and/or O-2 sequences in tandem. However, one of skill in the art can readily generate a vector containing more than three copies of these tetO sequences. For a discussion of the tet operator sequences, see, e.g., I. Kaffenberger, J Biol. Chem., 257:6805-6813 (1982); W. Hillen et al, J Mol. Biol, 172: 185-201 (1984); G. Klock et al, J Bacteriology, 161:326-332 (1985); C. Kleinschmidt et al, Biochem., 27: 1094-1104 (1988), and more recently, P. Orth et al, Nature Struct. Biol., 7:215-219 (2000).

least one tet operator sequence located 3' with respect to the TATA box in the CMV promoter. In yet another embodiment, the transcriptional regulatory sequence according to the invention comprises the human cytomegalovirus (hCMV) immediate early promoter and two tandem tet operator sequences located 3' with respect to the TATA box in the CMV promoter. In a yet more preferred embodiment, each of the tet operator sequences has the sequence CCCTATCAGTGATAGAG (SEQ ID NO:6). A typical transcription regulatory region suitable for use in the present invention comprising the hCMV minimal intermediate early promoter and two tet operator sequences downstream of the promoter has been described in WO9900510, the contents of which are incorporated herein by reference.

In yet another embodiment, the transcription regulatory sequence according to the invention comprises the sequence (SEQ ID NO:7)

```
  1 GCCCCATTGA CGCAAATGGG CGGTAGGCGT GTACGGTGGG AGGTCTATAT
 51 AAGCAGAGCT CTCCCTATCAGTGATAGA GATCTCCCTATC AGTGATAGAGA
```

The first promoter and the binding site for a transcriptional repressor are arranged so that the binding of the transcriptional repressor to said binding site inhibits the transcriptional activity of the promoter. Typically, this can achieved by positioning the binding site for a transcriptional repressor at a suitable distance from the TATA box in the promoter so that the repressor binds to the same side of the DNA helix as the TATA-binding protein. This is typically achieved when the binding site for the transcriptional repressor begins at a position between 6 and 100 nucleotides (and preferably between 6 and 24 nucleotides) downstream from the TATA element in the promoter region. Thus, in a preferred embodiment, the binding site for a transcriptional repressor is located downstream of the first promoter. The relative orientation between the promoter region and the binding site for a transcriptional repressor as well as the optimal distance between both regions in order to prevent transcription driven by the promoter when the transcriptional repressor is bound to the binding site can be determined by routine experimentation using a method as described in WO9900510. According to these methods, a plasmid comprising a reporter gene under operative control from a promoter and the binding site for a transcriptional repressor is introduced in a host cell and the transcriptional activity of the reporter gene is determined in a cell which expresses the transcriptional repressor. If the presence in the polynucleotides of a binding site for a transcriptional repressor inhibits the transcriptional activity of the promoter, no or minimal expression of the reporter gene should be observed. In the context of the present invention, the expression "that the binding of the transcriptional repressor to said binding site inhibits the transcriptional activity of the promoter" is to be understood that the placement of the binding of the transcriptional repressor in the vicinity of the promoter results in at least 50%, at least 60%, at least 70%, at least 80%, at least 90%, at least 95%, at least 96%, at least 97%, at least 98%, at least 99% or at least 100% of inhibition in the transcription of a gene operatively linked to the promoter when compared to the transcription driven by the promoter in the absence of a neighboring binding site for a transcriptional repressor.

In a preferred embodiment, the transcriptional regulatory sequence according to the invention comprises the human cytomegalovirus (hCMV) immediate early promoter and at wherein the underlined region corresponds to the CMV promoter and the double underlined regions correspond to the Tet operator sequences.

Expression Cassette

The second component of the all-in-one vector according to the invention is an expression cassette comprising a polynucleotide encoding a regulatable transcriptional repressor under the operative control of a second promoter wherein said regulatable transcriptional repressor is capable of specifically binding to the binding site in the transcriptional regulatory sequence in the absence but not in the presence of a ligand of said repressor.

The term "expression cassette" refers to a nucleic acid construct, generated recombinantly or synthetically, with a series of specified nucleic acid elements, which permit transcription of a particular nucleic acid in a target cell The term "regulatable transcriptional repressor" refers to a molecule capable of inhibiting the expression of a particular gene from a promoter in a regulatable manner, i.e. that it can be turned "on" or "off" regulated by the presence or absence of biotic or abiotic factors. In effect, the molecule "represses" the expression of the gene from its promoter in the presence or absence of a given inducer molecule, which is typically a ligand of said repressor. For example, the tet repressor is a protein that represses gene transcription of the tet operon upon binding to its cognate tet operator sequences within the operon promoter in the absence of a cognate ligand (tetracycline) but not in the presence of the ligand. Examples of inducible repressors include: chemically-regulated repressors, including repressors whose transcriptional activity is regulated by the presence or absence of alcohol, tetracycline, steroids, metal and other compounds; and physically-regulated repressors, including repressors whose transcriptional activity is regulated by the presence or absence of light and low or high temperatures. Examples chemically inducible repressors can have hormone-responsive elements (HREs), metal-responsive elements (MREs), heat shock-responsive elements (HSREs), tetracycline operator sequence (TetO) and interferon-responsive elements (IREs).

In a preferred embodiment, the regulatable transcriptional repressor is a Tet repressor. The term "Tet repressor", as used herein, refers to a protein occurring in nature or modified forms thereof which combines high affinity for its cognate DNA sequence (tetO) with sensitive induction by tetracycline (tc) and especially the more potent analogs doxycycline (dox) and anhydrotetracycline (ate). The Tet repressor regulate transcription from Tet operator sequences in prokaryotic cells in the absence or presence of tetracycline. The tetracycline-dependent transcriptional regulator binds to the tet operator in the absence of tetracycline or analog thereof (so-called "authentic tetracycline-dependent transcriptional activators" or "tTA") while in the presence of tetracycline the repressor does not longer bind to the cognate operator sequences.

Preferred tetracycline-dependent transcriptional regulators having said properties are disclosed in U.S. Pat. No. 5,464,758, U.S. Pat. No. 6,914,124, U.S. Pat. No. 5,789,156, U.S. Pat. No. 6,271,348, WO96/01313, or WO00/75347 which are herewith incorporated by reference. As used herein, "repression" of transcription is intended to mean a diminution in the level or amount of transcription of a target nucleic acid sequence compared to the level or amount of transcription prior to regulation by the transcriptional silencer protein. Transcriptional inhibition may be partial or complete.

The term "Tet repressor" includes wild-type repressor and mutated Tet repressors.

The term "wild-type Tet repressor" is intended to describe a protein occurring in nature which represses transcription from Tet operator sequences in prokaryotic cells in the absence of tetracycline. The term is intended to include repressors of different class types, such as but not limited to, TetR(A), TetR(B), TetR(C), TetR(D), TetR(E), TetR(G), TetR(H), TetR(J), and TetR(Z). In light of the high degree of sequence conservation (at least 80 percent) among members of each class of Tet repressor, a single member of each class of Tet repressor is used herein as representative of the entire class. Accordingly, the teaching of the present invention with respect to a specific member of a Tet repressor class is directly applicable to all members of that class.

As used herein, the TetR(A) class is represented by the Tet repressor carried on the Tnl721 transposon (Allmeir et al. (1992) Gene 111: 11-20; NCBI (National Library of Medicine, National Center for Biotechnology Information) accession number X61367 and database cross reference number (G1:) for encoded protein sequence GL48198).

The TetR(B) class is represented by a Tet repressor encoded by a TnlO tetracycline resistance determinant (Postle et al. (1984) Nucleic Acids Research 12(12): 4849-63, Accession No. X00694, G 43052).

The TetR(C) class is represented by the tetracycline repressor of the plasmid pSCIO1 (Brow et al. (1985) Mol. Biol. Evol 2(1): 1-12, Accession No. M36272, GL150496).

The TetR(D) class is represented by the Tet repressor identified in *Salmonella ordonez* (Allard et al. (1993) Mol. Gen. Genet. 237: 301-5, Accession No. X65876, GL49075).

The TetR(E) class is represented by a Tet repressor isolated from a member of Enterobacteriaceae (Tovar et al. (1988) Mol Gen. Genet. 215(1): 76-80, Accession No. M34933, GI: 155020).

The TetR(G) class is represented by a Tet repressor identified in *Nibrio anguillarum* (Zhao et al. (1992) Microbiol Immunol 36: 1051-60, Accession No. S52438, GT.262929).

The TetR(H) class is represented by a Tet repressor encoded by plasmid pMN1 11 isolated from *Pasteurella multocida* (Hansen et al. (1993) Antimicrob. Agents. Chemother. 37(12): 2699-705, Accession No. U00792, G 392872).

The TetR(J) class is represented by a Tet repressor cloned from *Proteus mirabilis* (Magalhaes et al. (1998) Biochim. Biophys. Acta. 1443(1-2): 262-66, Accession No. AF038993, GL4104706).

The TetR(Z) class is represented by a Tet repressor encoded by the pAG1 plasmid isolated from the gram-positive organism *Corynebacterium glutamicum* (Tauch et al. (2000) Plasmid 44(3): 285-91, Accession No. AAD25064, G 4583400).

Nucleotide and amino acid sequences of Tet repressors of the A, C, D and E classes are disclosed in Waters, S. H. et al. (1983) Nucl. Acids Res 11:6089-6105, Unger, B. et al. (1984) Gene 3: 103-108, Unger, B. et al. (1984) Nucl Acids Res. 12:7693-7703 and Tovar, K. et al. (1988) Mol. Gen. Genet. 215:76-80, respectively. These wild-type sequences can be mutated according to the teachings of the invention for use in the inducible regulatory system described herein.

The term "mutated Tet repressor" is intended to include polypeptides having an amino acid sequence which is similar to a wild-type Tet repressor but which derives from the wild-type repressor by substitution of one or more amino acids, deletion of one or more amino acids or addition of one or more amino acids and which substantially preserve their ability to interact with the Tet operator sequences in the absence of the tetracycline analog. The ability of a mutated Tet repressor to bind to the Tet operator sequences can be determined by the skilled person by routine experimentation by providing a cell comprising a nucleic acid molecule comprising a Tet operator sequence operatively linked to a reporter gene (e.g. the Lac repressor which controls the expression of a gene encoding an selectable marker (e.g., drug resistance). Binding of the mutated or variant Tet repressor to tet operator sequences in the host cell will inhibit expression of the Lac repressor in the absence of tetracycline, thereby inducing expression of the selectable marker gene. Cells expressing the marker gene are selected based upon the selectable phenotype (e.g., drug resistance).

The term "mutated Tet repressor" includes repressors that confers the ability of the inducer specific TetR to preferentially bind to a certain tetracycline analog or type of tetracycline analog. An inducer specific modified TetR has inducer affinity distinction between tetracycline analogs, wherein the modified TetR binds certain tetracycline analogs but not others. For instance, the mutated Tet repressor tetracycline analogs lacking the 4-dma grouping and does not bind tc or tc analogs with a 4-dma grouping Alternative to the above-described mutations, additional suitable mutated Tet repressors (e.g., having the desired functional properties described above) can be created by mutagenesis of a wild type Tet repressor and selection as described in U.S. Pat. No. 5,789,156 (Example 1). The nucleotide and amino acid sequences of wild-type class B Tet repressors are disclosed in Hillen, W. and Schollmeier, K. (1983) Nucl. Acids Res. 11:525-539 and Postle, K. et al. (1984) Nucl. Acids Res. 12:4849-4863. References for the nucleotide and amino acid sequences of wild-type class A, C, D and E type repressors are cited above. A mutated Tet repressor can be created and selected, for example as follows: a nucleic acid (e.g., DNA) encoding a wild-type Tet repressor is subjected to random mutagenesis and the resultant mutated nucleic acids are incorporated into an expression vector and introduced into a host cell for screening. A screening assay, e.g., which allows for selection of a Tet repressor which binds to a Tet operator sequence only in the absence of a substituted tetracycline compound can be used. For example, a library of mutated nucleic acids in an expression vector can be introduced into an *E. coli* strain in which Tet operator sequences control the expression of a gene encoding a Lac repressor and the Lac repressor controls the expression of a gene encoding an selectable marker (e.g., drug resistance). Binding of a Tet repressor to Tet operator sequences in the bacteria will inhibit expression of the Lac repressor, thereby inducing expression of the selectable marker gene. Cells expressing the marker gene are selected based upon the selectable phenotype (e.g., drug resistance). For wild-type Tet repressors, expression of the selectable marker gene will occur in the absence of tetracycline. A nucleic acid encoding a mutated Tet repressor may be selected using this system based upon the ability of the nucleic acid to induce expression of the selectable marker gene in the bacteria only in the presence of a substituted tetracycline compound.

Also comprised within the scope of the present invention are "chimeric tetracycline repressor" or "chimeric revTetR". As used herein, "chimeric tetracycline repressor" is intended to include polypeptides having an amino acid sequence comprising amino acid residues derived from more than one type of tetracycline repressor. The term is intended to include chimeric tetracycline repressors constructed from different class types, such as but not limited to, TetR(A), TetR(B), TetR(C), TetR(D), TetR(E), TetR(G), TetR(H), TetR(J), and TetR(Z). In certain embodiments, the chimeric tetracycline repressors of the present invention comprise an amino-terminal DNA-binding domain and a carboxy-terminal tetracycline binding domain, including but not limited to the corresponding domains of the TetR(A), TetR(B), TetR(C), TetR(D), TetR(E), TetR(G), TetR(H), TetR(J), and TetR(Z). Such chimeric tetracycline repressors further comprise at least one amino acid substitution that confers the reverse phenotype. A chimeric revTetR retains the DNA binding specificity of the DNA binding domain of a wild-type Tet repressor. Preferably, this reverse phenotype of the chimeric revTetR is displayed a eukaryote.

The transcriptional repressor according to the present invention may further comprise one or more copies of a nuclear localization signal. As used herein, the term "nuclear localization signal" means an amino acid sequence known to, in vivo, direct a protein disposed in the cytoplasm of a cell across the nuclear membrane and into the nucleus of the cell. This is particularly useful in the case of transcriptional repressors of bacterial origin when they are used in eukaryotic cells since they are devoid of naturally occurring NLSs. A variety of nuclear localization signals are known and selection of an appropriate sequence can be made based on the known properties of these various sequences. Representative NLSs include monopartite sequences such as that from SV40 large T antigen and the c-myc proto-oncogene. Bipartite signals are characterized as a small cluster of basic residues positioned 10-12 residues N-terminal to a monopartite-like sequence. An example of a bipartite nuclear localization signal is that from nucleoplasmin. In some embodiments, a NLS selected from the following list may be conjugated to the oligonucleotide: SV40 large T Antigen: PKKKRKV (SEQ ID NO: 8); Nucleoplasmin: KRPAAIK-KAGQ AKKKK (SEQ ID NO: 9); CBP80: RRRHS-DENDGGQPHKRRK (SEQ ID NO: 10); HIV-I Rev: RQARRNRRRWE (SEQ ID NO: 11); HTLV-I Rex: MPK-TRRRPRRSQRKRPPT (SEQ ID NO: 12); hnRNP A: NQSSNFGPMKGGNFGGRSSGP YGGGGQ YFAKPRN-QGGY (SEQ ID NO: 13); c-myc PAAKRVKLD (SEQ ID NO: 14) and rpL23a: VHSHKKKKIRTSPTFTTPKTLRL-RRQPKYPRKSAPRRNKLDHY (SEQ ID NO: 15). In one embodiment of the invention, the nuclear localization signal comprises the motif K(K/R)X(K/R) (SEQ ID NO: 16). In a specific embodiment, the nuclear localization signal is KRXR (SEQ ID NO: 17), wherein X is any amino acid.

The NLS may be present at any position in the transcriptional repressor, although it is preferably present at the C-terminus.

The regulatable transcriptional repressor is under the operative control of a second promoter.

The terms "under the operative control" and "operatively linked" are used herein interchangeably to refer to two nucleic acids are either physically linked or are functionally linked so that at least one of the nucleic acids can act on the other nucleic acid. The transcription control sequence of the present invention and a nucleic acid sequence to be expressed, e.g., a gene of interest, are operatively linked if the expression of the nucleic acid sequence can be governed by the said transcription control sequence. Accordingly, the transcription control sequence and the nucleic acid sequence to be expressed may be physically linked to each other, e.g., by inserting the transcription control sequence at the 5' end of the nucleic acid sequence to be expressed. Alternatively, the transcription control sequence and the nucleic acid to be expressed may be merely in physical proximity so that the transcription control sequence is functionally linked to the nucleic acid sequence to be expressed. The transcription control sequence and the nucleic acid to be expressed are, preferably, separated by not more than 1,500 bp, 500 bp, 300 bp, 100 bp, 80 bp, 60 bp, 40 bp, 20 bp, 10 bp or 5 bp.

The term "promoter" has been defined in detail in respect of the transcriptional regulatory sequence of the vector of the invention and is usually with the same meaning in the context of the expression cassette. The second promoter may be the same as the first promoter but both promoters must be in different regions of the vector, i.e. the first promoter and the second promoter are independent promoters. Suitable promoters for use as second promoters for regulating the expression of the transcriptional repressor may be any of the promoters mentioned above as suitable as first promoter. In a preferred embodiment, the second promoter is a promoter functional in mammalian cells. In a more preferred embodiment, the second promoter is the Spleen Focus Forming Virus (SFFV) Long Term Repeat (SFFV LTR) promoter (hereinafter SFFV promoter) as described by Joyner et al. (Proc. Natl. Acad. Sci. USA, 1982, 79: 1573-7). In another embodiment, the second promoter is the EF1α promoter.

Sequences Suitable for Expressing a Gene of Interest

The polynucleotides according to the present invention may further comprise regions adequate for inserting a polynucleotide of interest so that said polynucleotide is under operative control of the transcriptional regulatory region. In a preferred embodiment, the polynucleotide of the invention comprises a polylinker downstream of the transcriptional regulatory region. The terms "polylinker" and "multiple cloning site" are used herein interchangeably to refer to refer to a region of DNA that contains one or more commonly used restriction sites allowing the insertion of a DNA fragment (e.g., gene of interest) into the expression construct.

Alternatively, the polynucleotide according to the present invention may further comprise a polynucleotide of interest under operative control of the transcriptional regulatory region. The skilled person will appreciate that the polynucleotides of interest for use in the polynucleotides according to the present invention will depend on the intended use of the vector. Particularly preferred polynucleotides include reporter genes, when the polynucleotides of the invention are used as research tools or for imaging purposes, polynucleotides encoding polypeptides when the polynucleotides are used for gene therapy in diseases characterised by a lack of function of said polypeptide and polynucleotides which are capable of silencing the expression of target genes, adequate in those cases wherein the polynucleotides according to the invention are used for the treatment of diseases associated with an excessive expression of a given gene, either endogenous to the organism being treated or heterologous. Examples of polynucleotides of interest that can be inserted downstream of the transcriptional regulatory region are provided below in the context of the therapeutic and non-therapeutic uses of the polynucleotides of the invention.

Vectors, Host Cells and Viral Particles

In a further aspect, the invention relates to a vector comprising the polynucleotide according to the invention. The term "vector", as used herein, is intended to include a nucleic acid molecule capable of transporting another nucleic acid to which it has been linked. The term "vector", preferably, encompasses phage, plasmid, viral or retroviral vectors as well artificial chromosomes, such as bacterial or yeast artificial chromosomes. Moreover, the term also relates to targeting constructs which allow for random or site-directed integration of the targeting construct into genomic DNA. Such targeting constructs, preferably, comprise DNA of sufficient length for either homologous recombination or heterologous integration as described in detail below. The vector encompassing the transcription control sequence of the present invention, preferably, further comprises selectable markers for propagation and/or selection in a host.

A vector may be characterized by one or a small number of restriction endonuclease sites at which such DNA sequences may be cut in a determinable fashion without the loss of an essential biological function of the vector, and into which a DNA fragment may be spliced in order to bring about its replication and cloning. A vector may further contain a marker suitable for use in the identification of cells transformed with the vector. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

In a preferred embodiment of the vector of the present invention, said vector is an expression vector. More preferably, in the vector of the invention, the transcription control sequence is operatively linked to a nucleic acid sequence to be expressed. Such operative linkage, preferably, allows expression of the said nucleic acid sequence in eukaryotic cells or isolated fractions thereof. In principle, regulatory elements ensuring expression in eukaryotic cells, preferably mammalian cells, are well known in the art. They, preferably, comprise regulatory sequences ensuring initiation of transcription as comprised by the transcription control sequence of the present invention as well as poly-A signals ensuring termination of transcription and stabilization of the transcript. Additional regulatory elements may be included into the vector such as transcriptional as well as translational enhancers. In this context, suitable expression vectors are known in the art such as vectors derived from retroviruses including lentiviruses, adenovirus, cytomegalovirus, adeno-associated viruses, measles virus, vaccinia virus, herpes viruses, or bovine papilloma virus, may be used for delivery of the vector of the invention into targeted cell population. Methods which are well known to those skilled in the art can be used to construct recombinant viral vectors; see, for example, the techniques described in Sambrook, Molecular Cloning—A Laboratory Manual, Cold Spring Harbor Laboratory (1989) N.Y. and Ausubel, Current Protocols in Molecular Biology, Green Publishing Associates and Wiley Interscience, N.Y. (1994).

Among the different vectors that may be used as all-in-one vectors in the context of the invention, lentiviral vectors are preferred because they are one of the most promising vectors for gene transfer in primary human cells, they are highly efficient and do not express any viral gene that could alter normal cellular physiology.

As used herein, the term "lentivirus" refers to a group (or scientific genus) of retroviruses that in nature give rise to slowly developing disease due to their ability to incorporate into a host genome. Modified lentiviral genomes are useful as viral vectors for the delivery of a nucleic acid sequence to a cell. An advantage of lentiviruses for infection of cells is the ability for sustained transgene expression. These viruses include in particular Human Immunodeficiency Virus type 1 (HIV-1), Human Immunodeficiency Virus type 2 (HIV-2), Simian Immunodeficiency Virus (SIV), Feline Immunodeficiency Virus (FIV), Equine Infectious Anaemia Virus (EIAV), Bovine Immunodeficiency Virus (BIV), Visna Virus of sheep (VISNA) and Caprine Arthritis-Encephalitis Virus (CAEV). Lentiviral vectors are well known in the art (see, for example, Naldini et al., Science, 272(5259):263-267, 1996; Zufferey et al., Nat Biotechnol, 15(9):871-875, 1997; Blomer et al., J Virol, 71(9):6641-6649, 1997; U.S. Pat. Nos. 6,013,516 and 5,994,136). Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific. The recombinant lentiviruses according to the invention may be genetically modified in such a way that certain genes constituting the native infectious virus are eliminated and replaced with a nucleic acid sequence of interest to be introduced into the target cells.

The lentiviral vector can integrate into the genome of the host cell. The genetic material thus transferred is then transcribed and possibly translated into proteins inside the host cell. When the lentiviral vector is a non integrative lentiviral vector, the vector is present in episomal forms. The lentiviral vector according to the present invention, in addition to the transcriptional regulatory sequence and the expression cassette as described above, may further comprise additional elements which help to improve expression of the genes encoded within the vector.

- Regions required for the integrate of the vector into the genome of the target cell such as the Long-terminal repeats (LTRs) which flank the all-in-one vector defined herein. Thus, a lentiviral vector according to the invention preferably comprises a 5' LTR and a 3' LTR. "5' LTR" refers to a 5' retroviral or lentiviral long terminal repeat, which may or may not be modified from its corresponding native 5' LTR by deleting and/or mutating endogenous sequences and/or adding heterologous sequences. The 5' LTR may be natural or synthetic. "3' LTR" refers to a 3' retroviral or lentiviral long terminal repeat, which may or may not be modified from its corresponding native (i.e., that existing in the wild-type retrovirus) 3' LTR by deleting and/or mutating endogenous sequences and/or adding heterologous sequences. The 3' LTR may be natural or synthetic.
- An encapsidation sequence such as the lentiviral Psi (ψ) sequence,
- Sequences enhancing the RNA nuclear export, advantageous during the production, such as the sequence comprising the HIV-1 REV response element (RRE) sequence. Another sequence, usable in the context of the present invention, which enhances the RNA nuclear export, is the CTE sequence (Oh et al, 2007, Retrovirology. 2007 Jun. 5; 4:38.). These sequences are also useful for determining the copy number of the integrated lentiviral vectors.
- Sequences enhancing the nuclear import of the retrotranscribed viral DNA, such as the lentiviral cPPT CTS (flap) sequence from HIV-1. Other sequences, usable in the context of the present invention, enhancing DNA nuclear import are lentiviral cPPT CTS sequences from HIV-2, SIV, FIV, EIAV, BIV, VISNA and CAEV.
- Posttranscriptional regulation elements may be selected from Woodchuck hepatitis virus responsive element (WPRE), APP UTR5' region and TAU UTR3'.
- One or more insulator sequences selected from the group consisting of, for example, MAR, SAR, S/MAR, scs and scs' sequences.
- Additional transcriptional regulatory elements: These are regions which help to improve expression of the genes encoded within the vector. In particular, the vector may incorporate the wood-chuck hepatitis virus post-transcriptional regulatory element (WPRE) at the 3' untranslated region (Paterna et al., 2000, Gene Ther. 7: 1304-1311).

In another embodiment the lentiviral vector is another form of self-inactivating (SIN) vector as a result of a deletion in the 3' long terminal repeat region (LTR). Preferably, the vector contains a deletion within the viral promoter. The LTR of lentiviruses such as the HIV LTR contains a viral promoter. Although this promoter is relatively inefficient, when transactivated by e.g. tat, the promoter is efficient because tat-mediated transactivation increases the rate of transcription about 100 fold. However, the presence of the viral promoter can interfere with heterologous promoters operably linked to a transgene. To minimize such interference and better regulate the expression of transgenes, the lentiviral promoter may be deleted.

In a particular embodiment, the lentiviral vector comprises, in the 5' to 3' orientation:
  The 5' LTR (wild-type or modified)
  A Rev response element (RRE)
  a c polypurine tract (cPPT)
  the transcriptional regulatory region
  a polynucleotide of interest
  the expression cassette
  the WPRE transcriptional regulation element and
  the 3' LTR In another embodiment, the invention relates to a host cell which comprises a polynucleotide according to the present invention. As used herein, a "host cell" includes any cultivatable cell that can be modified by the introduction of heterologous DNA. Preferably, a host cell is one in which the transcriptional repressor encoded by the polynucleotide of the invention protein can be stably expressed, post-translationally modified, localized to the appropriate sub-cellular compartment, and made to engage the appropriate transcription machinery. The choice of an appropriate host cell will also be influenced by the choice of detection signal. For example, reporter constructs, as described below, can provide a selectable or screenable trait upon activation or inhibition of gene transcription in response to a transcriptional regulatory protein; in order to achieve optimal selection or screening, the host cell phenotype will be considered. A host cell of the present invention includes prokaryotic cells and eukaryotic cells. Prokaryotes include gram negative or gram positive organisms, for example, *E. coli* or *Bacilli*. It is to be understood that prokaryotic cells will be used, preferably, for the propagation of the transcription control sequence comprising polynucleotides or the vector of the present invention. Suitable prokaryotic host cells for transformation include, for example, *E. coli, Bacillus subtilis, Salmonella typhimurium*, and various other species within the genera *Pseudomonas, Streptomyces*, and *Staphylococcus*. Eukaryotic cells include, but are not limited to, yeast cells, plant cells, fungal cells, insect cells (e.g., baculovirus), mammalian cells, and the cells of parasitic organisms, e.g., trypanosomes. As used herein, yeast includes not only yeast in a strict taxonomic sense, i.e., unicellular organisms, but also yeast-like multicellular fungi of filamentous fungi. Exemplary species include *Kluyverei lactis, Schizosaccharomyces pombe*, and *Ustilaqo maydis*, with *Saccharomyces cerevisiae* being preferred. Other yeasts which can be used in practicing the present invention are *Neurospora crassa, Aspergillus niger, Aspergillus nidulans, Pichia pastoris, Candida tropicalis*, and *Hansenula polymorpha*. Mammalian host cell culture systems include established cell lines such as COS cells, L cells, 3T3 cells, Chinese hamster ovary (CHO) cells, embryonic stem cells, with BHK, HeK or HeLa cells being preferred. Eukaryotic cells are, preferably, used to for recombinant gene expression by applying the transcription control sequence or the expression vector of the present invention.

The host cell of the invention may be obtained by contacting a cell with a vector of the invention under conditions adequate for the incorporation of the vector into a host cell. The vector may be incorporated into a host cell by various techniques well known in the art. Suitable methods for nucleic acid delivery for transformation of a cell, a tissue or an organism for use with the current invention are believed to include virtually any method by which a nucleic acid (e.g., DNA) can be introduced into a cell, a tissue or an organism, as described herein or as would be known to one of ordinary skill in the art. Such methods include, but are not limited to, direct delivery of DNA such as by ex vivo transfection (Wilson et al., Science, 244:1344-1346, 1989, Nabel and Baltimore, Nature 326:711-713, 1987), optionally with Fugen (Roche) or Lipofectamine (Invitrogen), by injection (U.S. Pat. Nos. 5,994,624, 5,981,274, 5,945,100, 5,780, 448, 5,736,524, 5,702,932, 5,656,610, 5,589,466 and 5,580, 859, including microinjection (Harland and Weintraub, J. Cell Biol, 101: 1094-1099, 1985; U.S. Pat. No. 5,789,215; by electroporation (U.S. Pat. No. 5,384,253, Tur-Kaspa et al., Mol. Cell Biol, 6:716-718, 1986; Potter et al., Proc. Natl. Acad. Sci. USA, 81:7161-7165, 1984); by calcium phosphate precipitation (Graham and Van Der Eb, Virology, 52:456-467, 1973; Chen and Okayama, Mol Cell Biol, 7(8):2745-2752, 1987; Rippe et al., Mol. Cell Biol, 10:689-695, 1990); by using DEAE-dextran followed by polyethylene glycol (Gopal, Mol. Cell Biol, 5: 1188-1190, 1985); by direct sonic loading (Fechheimer et al., Proc. Natl. Acad. Sci. USA, 84:8463-8467, 1987); by liposome mediated transfection (Nicolau and Sene, Biochim. Biophys. Acta, 721:185-190, 1982; Fraley et al., Proc. Nat'l Acad. Sci. USA, 76:3348-3352, 1979; Nicolau et al., Methods Enzymol, 149: 157-176, 1987; Wong et al., Gene, 10:87-94, 1980; Kaneda et al., Science, 243:375-378, 1989; Kato et al., J Biol Chem., 266:3361-3364, 1991) and receptor-mediated transfection (Wu and Wu, Biochemistry, 27:887-892, 1988; Wu and Wu, J. Biol. Chem., 262:4429-4432, 1987); each incorporated herein by reference); and any combination of such methods.

In the particular case when the vector according to the invention is an integrative lentiviral vector, then the host cell is capable of integrating one or more copies of said vector in the genome. The expression level of the transcriptional repressor will depend on the strength of the promoter to which it is operatively linked and on the number of copies of the vector in the host cell. As shown in the present invention, a good inducibility and low leakiness in the expression of the polynucleotide of interest, the cells preferably contain at least 2 copies of the vector integrated. Moreover, maximal responsiveness can be reached when the cells have an average of 4 vectors copies of the vector. However, in those cases wherein the second promoter is a weak promoter, then a higher number of copies of the vector per genome may be required in order to achieve good inducibility, low leakiness and maximal responsiveness. In preferred embodiments, the host cell according to the invention contains at least 2, at least 3, at least 4, at least 5, at least 6, at least 7, at least 8, at least 9 and at least 10 copies of the polynucleotide of the invention integrated in the genome. In a still more preferred embodiment, the host cell according to the invention contains between 2 and 4 copies of the vector of the invention integrated in the genome. The vector contains, preferably, the SFFV promoter as second promoter.

In another embodiment, the invention relates to a lentiviral particle comprising the polynucleotide of the invention. The term "lentiviral particle", refers to a recombinant lentivirus which carries at least one gene or nucleotide sequence of interest, which is generally flanked by lentiviral LTRs. The lentivirus may also contain a selectable marker. The recombinant lentivirus is capable of reverse transcribing its genetic material into DNA and incorporating this genetic material into a host cell's DNA upon infection. The components of the particle may be modified with respect to the wild type lentivirus. For example, the Env proteins in the proteinaceous coat of the particle may be genetically modified in order to alter their targeting specificity or achieve some other desired function.

Lentiviral particles according to the invention can be obtained by contacting a suitable packaging cell with a lentiviral vector according to the invention and with one or more trans-complementing helper viruses which comprises the lentiviral genes needed for packaging of the lentiviral vector into vector capsids. In a preferred embodiment, the lentiviral particles are obtained using two helper plasmids. A first plasmid for trans-complementation provides a nucleic acid encoding the protein products of the gag and pol lentiviral genes and which is devoid of encapsidation sequence, of sequence encoding an envelope and, advantageously, is also devoid of lentiviral LTRs (the packaging plasmid). As a result, the sequences encoding gag and pol proteins are advantageously placed under control of a heterologous promoter, for example a viral, cellular, etc. promoter, which may be constitutive or regulated, weak or strong. This plasmid allows the expression of all the proteins necessary for the formation of empty virions, except the envelope glycoproteins. It is understood that the gag and pol genes may also be carried by different plasmids. A third plasmid provides a nucleic acid which allows the production of the chosen envelope (env) glycoprotein (the envelope plasmid). This vector is preferentially devoid of all lentiviral sequences.

Advantageously, the three vectors used do not contain any homologous sequence sufficient to allow a recombination. The nucleic acids encoding gag, pol and env may advantageously be cDNAs prepared according to conventional techniques, from sequences of the viral genes available in the prior art and on databases.

For the production of the non replicative lentiviruses, the vectors described above are introduced into competent cells and the viruses produced are harvested. The cells used may be any competent cell, preferably mammalian cell, for example animal or human cell, which is non pathogenic. Mention may, for example, be made of 293 cells, embryonic cells, fibroblasts, muscle cells, etc.

A preferred method for preparing a non replicative recombinant lentivirus, according to the invention, comprises transfecting a population of competent cells with a combination of vectors (two vectors, three vectors or more than three vectors) as described above, and recovering the viruses thus produced.

The lentiviruses of the invention may also be prepared, as explained previously, from an encapsidation cell line producing one or more gag, pol and env proteins.

Compositions or Kit-of-Parts

Although the polynucleotide of the invention is preferably used as an all-in-one of vector since it allows for a single step generation of the responsive primary cell lines and for gene therapy strategies, the invention also contemplates vector systems wherein the different elements of the all-in-one vector (the transcriptional regulatory sequence and the expression cassette) are provided in different polynucleotides. Thus, in another embodiment, the invention relates to a composition or kit-of-parts comprising (i) a first polynucleotide comprising transcriptional regulatory sequence comprising a first promoter and at least one binding site for a transcriptional repressor wherein said first promoter and said binding site are arranged so that the binding of the transcriptional repressor to said binding site inhibits the transcriptional activity of the promoter and (ii) a second polynucleotide comprising an expression cassette comprising a polynucleotide encoding a regulatable transcriptional repressor under the operative control of a second promoter wherein said regulatable transcriptional repressor is capable of specifically binding to the binding site in the transcriptional regulatory sequence in the absence but not in the presence of a ligand thereof.

The kit can be used to regulate the expression of a gene of interest (i.e., a nucleotide sequence of interest to be transcribed) which can be cloned under operative control of the transcription regulatory unit. Alternatively, eukaryotic cells which have nucleic acid encoding a transactivator and/or inhibitor fusion protein stably incorporated therein, such that the transactivator and/or inhibitor fusion protein are expressed in the eukaryotic cell, may be provided in the kit.

The term "kit" as used herein refers to a collection of the aforementioned compounds, means or reagents of the present invention which may or may not be packaged together. The components of the kit may be comprised by separate vials (i.e. as a kit of separate parts) or provided in a single vial. Moreover, it is to be understood that the kit of the present invention is to be used for practising the methods referred to herein above. It is, preferably, envisaged that all components are provided in a ready-to-use manner for practising the methods referred to above. Further, the kit preferably contains instructions for carrying out the said methods. The instructions can be provided by a users manual in paper- or electronic form. For example, the manual may comprise instructions for interpreting the results obtained when carrying out the aforementioned methods using the kit of the present invention.

In one embodiment, the kit includes a carrier means having in close confinement therein at least two container means: a first container means which contains the polynucleotide comprising the regulatable transcriptional sequence and a second container means which contains the expression cassette. The first polynucleotide typically comprises a cloning site for introduction of a nucleotide sequence to be transcribed (optionally including an operatively linked minimal promoter sequence) and at least one operatively linked tet operator sequence. The term "cloning site" is intended to encompass at least one restriction endonuclease site. Typically, multiple different restriction endonuclease sites (e.g., a polylinker) are contained within the nucleic acid.

The terms "polynucleotide", "transcriptional regulatory sequence", "promoter", "binding site for a transcriptional repressor", "expression cassette" and "regulatable transcriptional repressor" and "operative control" have been described in detail in the context of the polynucleotide of the invention and are used with the same meaning in the context of the composition or kit-of-parts of the invention.

In a preferred embodiment, the first and the second promoter are different promoters. In another preferred embodiment, the first promoter is the CMV immediate early promoter. In another embodiment, the binding site for a transcriptional repressor is a binding site for the tetracycline repressor and wherein the regulatable transcriptional repressor is the tetracycline repressor. In yet another embodiment, the binding site for the tetracycline repressor is a TetO operator sequence. In another embodiment, the binding site for the transcriptional repressor is downstream of the first promoter. In another embodiment, the second promoter is the SFFV promoter. In yet another embodiment, the composition or kit-of-parts of the invention further comprises a polynucleotide of interest under operative control of the transcriptional regulatory sequence. Suitable polynucleotides of interest are defined below in the context of the uses of the compositions and kits-of-parts of the invention. In another embodiment, the first and/or the second promoter are provided forming part of a vector. In another embodiment, the said vector is a lentiviral vector. In yet another embodiment, the lentiviral vector is an integrative lentiviral vector. The terms "vector", "lentiviral vector" and "integrative lentiviral vector" have been described in detail above in respect of the polynucleotide of the invention.

In another embodiment, the composition or kit-of-parts of the invention further comprises a ligand of the transcriptional repressor capable which, when bound to the repressor, results in the inactive repressor which is no longer capable of binding to its binding site in the transcriptional regulatory sequence. In the particular case wherein the transcriptional repressor is a tetracycline repressor, the ligand is tetracycline or a tetracycline analog. As used herein, "tetracycline analog" is intended to include compounds which are structurally related to tetracycline and which bind to the Tet repressor referred to herein below with a IQ of at least about 10−6 M. Preferably, the tetracycline analog binds with an affinity of about 10−9 M or greater. Preferred tetracycline analogs are anhydrotetracycline (ate), doxycycline (dox), chlorotetracycline, oxytetracycline, or deoxytetracycline. Further analogs are disclosed by Hlavka and Boothe, "The Tetracyclines," in Handbook of Experimental Pharmacology 78, R. K. Blackwood et al. (eds.), Springer-Verlag, Berlin, N.Y., 1985; Mitscher, "The Chemistry of the Tetracycline Antibiotics", Medicinal Research 9, Dekker, N.Y., 1978; Noyee Development Corporation, "Tetracycline Manufacturing Processes" Chemical Process Reviews, Park Ridge, N.J., 2 volumes, 1969; Evans, "The Technology of the Tetracyclines," Biochemical Reference Series 1, Quadrangle Press, New York, 1968; and Dowling, "Tetracycline," Antibiotic Monographs, no. 3, Medical Encyclopedia, New York, 1955. In addition, tetracycline analogs encompass those which are disclosed in WO2007/133797 and WO2007/133798.

The polynucleotides which form the compositions or kits-of-parts according to the invention may be provided as expression vectors as defined above and, more in particular, as lentiviral expression vectors. In this case, the polynucleotides may further comprise one or more elements selected from the group consisting of:

Long-terminal repeats (LTRs) at the 5' or 3' ends

An encapsidation sequence such as the lentiviral Psi (ψ) sequence,

A sequence enhancing the RNA nuclear export (e.g., the RRE sequence)

A sequence enhancing the nuclear import of the retrotranscribed viral DNA (e.g, the cPPT sequence).

One or more post-transcriptional regulation elements such as the Woodchuck hepatitis virus responsive element (WPRE)

An insulator sequence selected from the group consisting of for example, MAR, SAR, S/MAR, scs and scs' sequences.

Method for Regulating the Expression of a Nucleic Acid Sequence of Interest

In a host cell which carries a transcriptional regulatory sequence according to the invention, a polynucleotide sequence operatively linked to the transcriptional regulatory sequence and an expression cassette comprising a polynucleotide encoding a regulatable transcriptional repressor under the operative control of a second promoter allows high level transcription of the nucleotide sequence operatively linked to the transcriptional regulatory sequence in the presence of a ligand of the regulatable transcriptional repressor, whereas transcription does not occur in the absence of the ligand of the regulatable transcriptional repressor. The level of basal transcription of the nucleotide sequence may vary depending upon the host cell and site of integration of the sequence, but is generally quite low or even undetectable in the absence of a ligand of the transcriptional repressor. In order to induce transcription in a host cell, the host cell is contacted with a ligand for the transcriptional repressor wherein said regulatable transcriptional repressor is capable of specifically binding to the binding site in the transcriptional regulatory sequence in the absence but not in the presence of a ligand thereof. Thus, in another aspect, the invention relates to a method for regulating the expression of a nucleic acid sequence of interest comprising the steps of
(i) providing a host cell selected from the group consisting of:
   (a) a host cell comprising a polynucleotide according to the invention wherein the nucleic acid of interest is operatively linked to the first promoter in said polynucleotide and
   (b) a host cell comprising the first and second polynucleotides of the composition or kit-of-parts according to the invention wherein the nucleic acid is operatively linked to the first promoter of the first polynucleotide
and
(ii) contacting said host cell which with a ligand for the transcriptional repressor wherein said ligand is capable of binding to the transcriptional repressor producing an inactive repressor which is released from its binding site in the transcriptional regulatory sequence thereby allowing the transcription of the nucleic acid driven by the first promoter.

In order to be able to express a polynucleotide of interest, the polynucleotides, compositions and kits-of-parts according to the invention are modified so as to incorporate said polynucleotide of interest under operative control of the transcriptional regulatory sequence.

In a preferred embodiment, the binding site for a transcriptional repressor is a binding site for the tetracycline repressor, wherein the regulatable transcriptional repressor is the tetracycline repressor and wherein the ligand is tetracycline or an analog thereof. The term "tetracycline analog" has been defined in detail above.

To induce gene expression in a cell in vitro, the cell is contacted with the tetracycline or an analog thereof by culturing the cell in a medium containing the ligand. When culturing cells in vitro in the presence of the tetracycline or an analog thereof, a preferred concentration range for the inducing agent is between about 10 and about 1000 ng/ml. The tetracycline or analog thereof compound can be directly added to media in which cells are already being cultured, or more preferably for high levels of gene induction, cells are harvested from substituted tetracycline compound-free media and cultured in fresh media containing the desired substituted tetracycline compound. For example, mammalian, yeast or fungal cells can be modified to contain these nucleic acid molecules components as described herein. The modified mammalian, yeast or fungal cells can then be cultured by standard fermentation techniques in the presence of Tc or an analogue thereof to induce expression of the gene and produce the protein of interest. Accordingly, the invention provides a production process for isolating a protein of interest when the protein is toxic for the cells. In the process, a host cell (e.g., a yeast or fungus), into which has been introduced a polynucleotide according to the invention or a composition of polynucleotides according to the invention is grown at production scale in a culture medium in the absence of tetracycline. Once the culture reaches a peak, the addition of tetracycline or a tetracycline analogue stimulates transcription of the nucleotides sequence encoding the protein of interest (i.e., the nucleotide sequence operatively linked to the tet operator sequence(s)) and the protein of interest is isolated from harvested host cells or from the culture medium. Standard protein purification techniques can be used to isolate the protein of interest from the medium or from the harvested cells.

To induce gene expression in vivo, cells within in a subject are contacted with the tetracycline or analog thereof by administering the compound to the subject. The invention also provides for large scale production of a protein of interest in animals, such as in transgenic farm animals. Advances in transgenic technology have made it possible to produce transgenic livestock, such as cattle, goats, pigs and sheep (reviewed in Wall, R. J. et al. (1992) J. Cell. Biochem. 49:113-120; and Clark, A. J. et al. (1987) Trends in Biotechnology 5:20-24). Accordingly, transgenic livestock carrying in their genome the components of the inducible regulatory system of the invention can be constructed, wherein a gene encoding a protein of interest is operatively linked to at least one tet operator sequence. Gene expression, and thus protein production, is induced by administering certain Tc (or analogue thereof) to the transgenic animal. Protein production can be targeted to a particular tissue by incorporating into the transcriptional regulatory sequence in the polynucleotide of the invention an appropriate tissue-specific regulatory elements which limits expression of the gene of interest to certain cells. For example, a mammary gland-specific regulatory element, such as the milk whey promoter (U.S. Pat. No. 4,873,316 and European Application Publication No. 264,166), can be linked to the transactivator transgene to limit expression of the transactivator to mammary tissue. Thus, in the presence of Tc (or analogue), the protein of interest will be produced in the mammary tissue of the transgenic animal. The protein can be designed to be secreted into the milk of the transgenic animal, and if desired, the protein can then be isolated from the milk. In an exemplary embodiment, when the inducing agent is administered to a human or animal subject, the dosage is adjusted to preferably achieve a serum concentration between about 0.0005 and 1.0 µg/ml. The tetracycline or analogue thereof can be administered to a subject by any means effective for achieving an in vivo concentration sufficient for gene induction. Examples of suitable modes of administration include oral administration (e.g., dissolving the inducing agent in the drinking water), slow release pellets and implantation of a diffusion pump. To administer the substituted tetracycline compounds of the invention to a transgenic plant, the inducing agent can be dissolved in water administered to the plant.

The expression of a polynucleotide of interest can be carried out in any cell wherein the first and second promoters are functional. In a preferred embodiment, the cell is a mesenchymal stem cell. As used herein, As used herein the term "mesenchymal stem cell" (also referred to herein as "MSC") shall be taken to mean a cell which is capable of giving rise to multiple different types of cell, originally derived from the mesenchyme. In a preferred embodiment, the mesenchymal stem cell is a human mesenchymal stem cell.

The term "modulating the concentration of a tetracycline or analog thereof" as used herein means "altering the concentration of the tetracycline or analog thereof". Specifically, if a tetracycline-dependent transcriptional regulator which binds to the tet operator in the presence of tetracycline or analog thereof is to be used in the method of the present invention, the expression of the nucleic acid to be expressed can be achieved by adding de novo an amount of tetracycline or by increasing the amount of tetracycline present in the host cell, plant or non-human transgenic animal. Vice versa, if a tetracycline-dependent transcriptional regulator which binds to the tet operator in the absence of tetracycline or analog thereof is to be used, the tetracycline amount present in the host cell, plant or non-human transgenic animal shall be lowered or tetracycline may be withdrawn entirely. Tetracycline or an analog thereof may be delivered to the host cell, preferably, via the culture medium which comprises the host cells. In the case of plants, tetracycline or an analog thereof may be delivered to the individual cells of the plant or non-human transgenic animal by water or nutrient supply or via infusions. These techniques are well known to the person skilled in the art and can be adopted for individual conditions without further ado.

Uses of the Polynucleotide, Vectors and Lentiviral Particles of the Invention

The regulatable gene expression system of the invention has numerous advantages properties that make it particularly suitable for application to gene therapy. For example, the system provides an "on"/"off" switch for gene expression that allows for regulated dosing of a gene product in a subject. There are several situations in which it may be desirable to be able to provide a gene product at specific levels and/or times in a regulated manner, rather than simply expressing the gene product constitutively at a set level. For example, a gene of interest can be switched "on" at fixed intervals (e.g., daily, alternate days, weekly, etc.) to provide the most effective level of a gene product of interest at the most effective time. The level of gene product produced in a subject can be monitored by standard methods (e.g., direct monitoring using an immunological assay such as ELISA or RIA or indirectly by monitoring of a laboratory parameter dependent upon the function of the gene product of interest, e.g., blood glucose levels and the like). This ability to turn "on" expression of a gene at discrete time intervals in a subject while also allowing for the gene to be kept "off" at other times avoids the need for continued administration of a gene product of interest at intermittent intervals. This approach avoids the need for repeated injections of a gene product, which may be painful and/or cause side effects and would likely require continuous visits to a physician. In contrast, the system of the invention avoids these drawbacks. Moreover, the ability to turn "on" expression of a gene at discrete time intervals in a subject allows for focused treatment of diseases which involve "flare ups" of activity (e.g., many autoimmune diseases) only at times when treatment is necessary during the acute phase when pain and symptoms are evident. At times when such diseases are in remission, the expression system can be kept in the "off" state. Thus, in another aspect, the invention relates to a polynucleotide according to the invention, a vector according to the invention, a lentiviral particle according to the invention or a composition or kit-of-parts according to the invention for use in medicine.

Gene Therapy

The methods of the invention may be used in gene therapy approaches, in treatments for either genetic or acquired diseases. The general approach of gene therapy involves the introduction of nucleic acid into cells such that one or more gene products encoded by the introduced genetic material are produced in the cells to restore or enhance a functional activity. For reviews on gene therapy approaches see Anderson, W. F. (1992) Science 256:808-813; Miller, A. D. (1992) Nature 357:455-460; Friedmann, T. (1989) Science 244: 1275-1281; and Cournoyer, D., et al. (1990) Curr. Opin. Biotech. 1:196-208). Genes of particular interest to be expressed in cells of a subject for treatment of genetic or acquired diseases include those encoding adenosine deaminase, Factor VIII, Factor X, dystrophin, beta-globin, LDL receptor, CFTR, insulin, erythropoietin, anti-angiogenesis factors, growth hormone, glucocerebrosidase, beta-glucouronidase, $\alpha$1-antitrypsin, phenylalanine hydroxylase, tyrosine hydroxylase, ornithine transcarbamylase, arginosuccinate synthetase, UDP-glucuronysyl transferase, apoAl, TNF, soluble TNF receptor, interleukins (e.g., IL-2), interferons (e.g., $\alpha$- or $\gamma$-IFN) and other cytokines and growth factors. Cells types which can be modified for gene therapy purposes include hematopoietic stem cells, myoblasts, hepatocytes, lymphocytes, skin epithelium and airway epithelium. For further descriptions of cell types, genes and methods for gene therapy see e.g., Wilson, J. M et al. (1988) Proc. Natl Acad. Sci. USA 85:3014-3018; Armentano, D. et al. (1990) Proc. Natl. Acad. Sci. USA 87:6141-6145; Wolff, J. A. et al. (1990) Science 247:1465-1468; Chowdhury, J. R. et al. (1991) Science 254:1802-1805; Ferry, N. et al (1991) Proc. Natl. Acad. Sci. USA 88:8377-8381; Wilson, J. M. et al. (1992) J. Biol Chem. 267:963-967; Quantin, B. et al (1992) Proc. Natl. Acad. Sci. USA 89:2581-2584; Dai, Y. et al. (1992) Proc. Natl. Acad. Sci. USA 89:10892-10895; van Beusechem, V. W. et al. (1992) Proc. Natl. Acad. Sci. USA 89:7640-7644; Rosenfeld, M. A. et al. (1992) Cell 68:143-155; Kay, M. A. et al. (1992) Human Gene Therapy 3:641-647; Cristiano, R. J. et al. (1993) Proc. Natl. Acad. Sci. USA 90:2122-2126; Hwu, P. et al. (1993) J. Immunol. 150:4104-4115; and Herz, J. and Gerard, R. D. (1993) Proc. Natl. Acad. Sci. USA 90:2812-2816.

Gene therapy applications of particular interest in cancer treatment include overexpression of a cytokine gene (e.g., TNF-$\alpha$) in tumor infiltrating lymphocytes or ectopic expression of cytokines in tumor cells to induce an anti-tumor immune response at the tumor site, expression of an enzyme in tumor cells which can convert a non-toxic agent into a toxic agent, expression of tumor specific antigens to induce an anti-tumor immune response, expression of tumor suppressor genes (e.g., p53 or Rb) in tumor cells, expression of a multidrug resistance gene (e.g., MDR1 and/or MRP) in bone marrow cells to protect them from the toxicity of chemotherapy.

Gene therapy applications that may particularly benefit from this ability to modulate gene expression during discrete time intervals include the following non-limiting examples:

Rheumatoid arthritis—genes which encode gene products that inhibit the production of inflammatory cytokines (e.g., TNF, IL-1 and IL-12) can be expressed in subjects. Examples of such inhibitors include soluble forms of a receptor for the cytokine. Additionally or alternatively, the cytokines IL-10 and/or IL-4 (which stimulate a protective Th2-type response) can be expressed. Moreover, a glucocorticomimetic receptor (GCMR) can be expressed.

Hypopituitarism—the gene for human growth hormone can be expressed in such subjects only in early childhood, when gene expression is necessary, until normal stature is achieved, at which time gene expression can be downregulated.

Wound healing/Tissue regeneration—Factors (e.g., growth factors, angiogenic factors, etc.) necessary for the healing process can be expressed only when needed and then downregulated.

Anti-Cancer Treatments—Expression of gene products useful in anti-cancer treatment can be limited to a therapeutic phase until retardation of tumor growth is achieved, at which time expression of the gene product can be downregulated. Possible systemic anti-cancer treatments include use of tumor infiltrating lymphocytes which express immunostimulatory molecules (e.g., IL-2, IL-12 and the like), angiogenesis inhibitors (PF4, IL-12, etc.), Her-regulin, Leukoregulin (see PCT Publication No. WO 85/04662), and growth factors for bone marrow support therapy, such as G-CSF, GM-CSF and M-CSF. Regarding the latter, use of the regulatory system of the invention to express factors for bone marrow support therapy allows for simplified therapeutic switching at regular intervals from chemotherapy to bone marrow support therapy (similarly, such an approach can also be applied to AIDS treatment, e.g., simplified switching from anti-viral treatments to bone marrow support treatment). Furthermore, controlled local targeting of anti-cancer treatments are also possible. For example, expression of a suicide gene by a regulator of the invention, wherein the regulator itself is controlled by, for example, a tumor-specific promoter or a radiation-induced promoter.

Viral diseases—Expression of trans-dominant negative viral transactivation proteins, such as trans-dominant negative tat and rev mutants for HEV or trans-dominant ICp4 mutants for HSV (see e.g., Balboni, P. G. et al. (1993) J. Med. Virol. 41:289-295; Liem, S. E. et al (1993) Hum. Gene Ther. 4:625-634; Malim, M. H. et al. (1992) J. Exp. Med. 176:1197-1201; Daly, T J. et al (1993) Biochemistry 32:8945-8954; and Smith, C A. et al. (1992) Virology 191:581-588), expression of trans-dominant negative envelope proteins, such as env mutants for HEV (see e.g., Steffy, K. R. et al. (1993) J. Virol 67:1854-1859), intracellular expression of antibodies, or fragments thereof, directed to viral products ("internal immunization", see e.g., Marasco, W. A. et al (1993) Proc. Natl. Acad. Sci. USA 90:7889-7893) and expression of soluble viral receptors, such as soluble CD4. Additionally, the system of the invention can be used to conditionally express a suicide gene in cells, thereby allowing for elimination of the cells after they have served an intended function. For example, cells used for vaccination can be eliminated in a subject after an immune response has been generated the subject by inducing expression of a suicide gene in the cells by administering Tc or a Tc analogue to the subject.

Benign prostatic hypertrophy—Similar to the above, a suicide gene can be regulated by a regulator of the invention, wherein the regulator itself is controlled by, for example, a prostate-specific promoter.

Hemophilia: Factor XIII and EX (e.g., expression can be elevated during times of risk of injury, such as during sports);

Diabetes: insulin or amylin (as needed, depending on the state of disease in the subject, diet, etc.);

Erythrocytopenia: erythropoietin (as needed, e.g., at end-stage renal failure);

Artherosclerosis or gene therapy in liver: Low-density lipoprotein receptor (LDLr) or very low-density lipoprotein receptor (VLDLr) (e.g., using ex vivo implants).

Alzheimer's disease: Fine tuning of the expression of choline acetyl transferase (ChAT) to restore acetylcholine levels, neurotrophic factors (e.g., NGF, BDNGF and the like) and/or complement inhibitors (e.g., sCR1, sMCP, sDAF, sCD59 etc.) can be accomplished.

Parkinson's disease: Fine tuning of the expression of tyrosine hydroxylase (TH) to increase levodopa and dopamine levels.

In another embodiment, the regulatory proteins of the invention are used to express angiogenesis inhibitors) from within a tumor via a transgene regulated by the system of the invention. Expression of angiogenesis inhibitors in this manner may be more efficient than systemic administration of the inhibitor and would avoid any deleterious side effects that might accompany systemic administration. In particular, restricting angiogenesis inhibitor expression to within tumors could be particularly useful in treating cancer in children still undergoing angiogenesis associated with normal cell growth.

In another embodiment, high level regulated expression of cytokines may represent a method for focusing a patients own immune response on tumor cells. Tumor cells can be transduced to express chemoattractant and growth promoting cytokines important in increasing an individual's natural immune response. Because the highest concentrations of cytokines will be in the proximity of the tumor, the likelihood of eliciting an immunological response to tumor antigens is increased. A potential problem with this type of therapy is that those tumor cells producing the cytokines will also be targets of the immune response and therefore the source of the cytokines will be eliminated before eradication of all tumor cells can be certain. To combat this, expression of viral proteins known to mask infected cells from the immune system can be placed under regulation, along with the cytokine gene(s), in the same cells. One such protein is the E1 9 protein from adenovirus (see e.g., Cox, Science 247:715). This protein prevents transport of class I HLA antigens to the surface of the cell and hence prevents recognition and lysis of the cell by the host's cytotoxic T cells. Accordingly, regulated expression of E1 9 in tumor cells could shield cytokine producer cells from cytotoxic T cells during the onset of an immune response provoked by cytokine expression. After a sufficient period of time has elapsed to eradicate all tumor cells but those expressing E1 9, E1 9 expression can be turned off, causing these cells then to fall victim to the provoked anti-tumor immune response.

The ability to express a suicide gene (e.g., an apoptosis gene, TK gene, etc) in a controlled manner using the regulatory system of the invention adds to the general safety and usefulness of the system. For example, at the end of a desired therapy, expression of a suicide gene can be triggered to eliminate cells carrying the gene therapy vector, such as cells in a bioinert implant, cells that have disseminated beyond the intended original location, etc. Moreover, if a transplant becomes tumorigenic or has side effects, the cells can be rapidly eliminated by induction of the suicide gene.

In certain gene therapy situations, it may be necessary or desirable to take steps to avoid or inhibit unwanted immune reactions in a subject receiving treatment. To avoid a reaction against the cells expressing the therapeutic gene product, a subject's own cells are generally used, when possible, to express the therapeutic gene product, either by in vivo modification of the subject's cells or by obtaining cells from the subject, modifying them ex vivo and returning them to the subject. In situations where allogeneic or xenogeneic cells are used to express a gene product of interest, the regulatory system of the invention, in addition to regulating a therapeutic gene, can also be used to regulate one or more genes involved in the immune recognition of the cells to inhibit an immune reaction against the foreign cells. For example, cell-surface molecules involved in recognition of a foreign cell by T lymphocytes can be downmodulated on the surface of a foreign cell used for delivery of a therapeutic gene product, such as by regulated expression in the foreign cell of a ribozyme which cleaves the mRNA encoding the cell-surface molecule. Particularly preferred cell surface molecules which can be down-modulated in this manner to inhibit an unwanted immune response include class I and/or class II major histocompatibility complex (MHC) molecules, costimulatory molecules (e.g., B7-1 and/or B7-2), CD40, and various "adhesion" molecules, such as ICAM-1 or ICAM-2. Using approaches described herein for independent but coordinate regulation of multiple genes in the same cell, the down-regulation of expression of a cell-surface molecule(s) in a host cell can be coordinated with the up-regulation of expression of a therapeutic gene. Accordingly, after therapy is completed and expression of the therapeutic gene is halted, expression of the endogenous cell surface molecule(s) can be restored to normal.

Expression of Inhibitory RNAs

In another embodiment, the invention relates to recombinant vectors for inducible and/or tissue specific expression of nucleic acid molecules, e.g., double-stranded RNA molecules, that interfere with the expression of a target gene using methods known in the art. In this embodiment, a coding region encoding a target-gene-specific antisense RNA is operatively associated with the transcriptional regulatory region so that the binding of the tetracycline or analog thereof to the operator sequence results in the expression of the antisense RNA. In various aspects of this embodiment, the level of expression of an antisense RNA molecule, and translation of a target gene mRNA inhibited by the antisense RNA molecule, may be modulated by the concentration of tetracyline or its analog, the level of expression of the inducer specific TetR protein, and/or the temperature. In a particular aspect of this embodiment, the target gene corresponds to one copy of a duplicated gene in a prokaryotic organism, thereby allowing the construction of a host cell that can be functionally haploid for that gene product. Such organisms are particularly useful for the detection of antimicrobial agents active against the encoded target gene product.

As used herein, the term "RNA interference" or "RNAi" refers to selective intracellular degradation of RNA used to silence expression of a selected target gene. RNAi is a process of sequence-specific, post-transcriptional gene silencing in organisms initiated by double-stranded RNA (dsRNA) that is homologous in sequence to the gene to be silenced. The RNAi technique involves small interfering RNAs (siRNAs) that are complementary to target RNAs (encoding a gene of interest) and specifically destroy the known mRNA, thereby diminishing or abolishing gene expression. RNAi is mediated by small interfering RNAs (siRNAs). The term "small interfering RNA" or "siRNA" refers to a nucleic acid molecule which is a double stranded RNA agent that is complementary to i.e., able to base-pair with, a portion of a target RNA (generally mRNA). siRNA acts to specifically guide enzymes in the host cell to cleave the target RNA. By virtue of the specificity of the siRNA sequence and its homology to the RNA target, siRNA is able to cause cleavage of the target RNA strand, thereby inactivating the target RNA molecule. The complementary regions of the siRNA allow sufficient hybridization of the siRNA to the target RNA and thus mediate RNAi. In mammalian cells, siRNAs are approximately 21-25 nucleotides in length. The siRNA sequence needs to be of sufficient length to bring the siRNA and target RNA together through complementary base-pairing interactions. The siRNA used with the Tet expression system of the invention may be of varying lengths. The length of the siRNA is preferably greater than or equal to ten nucleotides and of sufficient length to stably interact with the target RNA; specifically 15-30 nucleotides; more specifically any integer between 15 and 30 nucleotides, such as 15, 16, 17, 18, 19, 20, 21, 22, 23, 24, 25, 26, 27, 28, 29, and 30. By "sufficient length" is meant an oligonucleotide of greater than or equal to 15 nucleotides that is of a length great enough to provide the intended function under the expected condition. By "stably interact" is meant interaction of the small interfering RNA with target nucleic acid (e.g., by forming hydrogen bonds with complementary nucleotides in the target xinder physiological conditions).

In addition to the RNAi, ribozymes can be expressed in a controlled manner in a subject for therapeutic purposes. For example, a ribozyme can be designed which discriminates between a mutated form of a gene and a wild-type gene. Accordingly, a "correct" gene (e.g., a wild-type p53 gene) can be introduced into a cell in parallel with introduction of a regulated ribozyme specific for the mutated form of the gene (e.g., a mutated endogenous p53 gene) to remove the defective mRNA expressed from the endogenous gene. This approach is particularly advantageous in situations in which a gene product from the defective gene would interfere with the action of the exogenous wild-type gene.

Animal Models of Human Disease

The polynucleotides, vectors, viral particles, compositions and kit-of-parts of the invention can be used to stimulate the expression of specific genes in animals to mimic the pathophysiology of human disease to thereby create animal models of human disease. For example, in a host animal, a gene of interest thought to be involved in a disease can be placed under the transcriptional control of one or more transcriptional regulatory sequence (e.g., by homologous recombination, as described herein). Such an animal can be mated to a second animal carrying the transcriptional repressor under the control of the second promoter, to create progeny that carry both polynucleotides. Expression of the gene of interest in these progeny can be modulated using a tetracycline or analog thereof. Alternatively, expression of the gene of interest can be down modulated using silencing molecules specific for the target gene under the control of the transcriptional regulatory sequence. Such an approach may be advantageous over gene "knock out" by homologous recombination to create animal models of disease, since the regulated system described herein allows for control over both the levels of expression of the gene of interest and the timing of when gene expression is down- or up-regulated.

Imaging of Regulated Gene Expression In Vivo

The methods of the invention can be employed in combination with invasive or more preferably, non-invasive imaging techniques, to monitor regulated gene expression in cells, cell lines and/or living subjects. For example, both a reporter gene (e.g., luciferase, GFP, CAT, etc.) and a nucleotide sequence of interest may be placed under the control of a transcriptional regulatory sequence, thereby rendering expression of the reporter gene and nucleotide sequence of interest responsive to a ligand of the transcriptional repressor. Through use of such genetic constructs, transgenic animals and cell lines may be derived within which expression and/or activity of a reporter gene such as luciferase serves as an indirect, non-invasive marker of the expression of the tet operator-linked nucleotide sequence. Use of such methods for implementation of non-invasive imaging in living subjects is described in Hasan, M T et al. Genesis 29(3):116-22. The term "indicator gene" or "reporter gene" generically refers to an expressible (e.g., able to transcribed and (optionally) translated) DNA sequence which is expressed in response to the activity of a transcriptional regulatory protein. Indicator genes include unmodified endogenous genes of the host cell, modified endogenous genes, or a reporter gene of a heterologous construct, e.g., as part of a reporter gene construct. In a preferred embodiment, the level of expression of an indicator gene produces a detectable signal. Examples of reporter genes include, but are not limited to CAT (chloramphenicol acetyl transferase) (Alton and Napnek, 1979, Nature 282: 864-869) luciferase, and other enzyme detection systems, such as beta-galactosidase; firefly luciferase (deWet et al. (1987), Mol. Cell Biol. 7:725-737); bacterial luciferase (Engebrecht and Silverman (1984), PNAS 1: 4154-4158; Baldwin et al. (1984), Biochemistry 23: 3663-3667); alkaline phosphatase (Toh et al. (1989) Eur. J. Biochem. 182: 231-238, Hall et al. (1983) J. Mol. Appl Gen. 2: 101), hximan placental secreted alkaline phosphatase (Cullen and Malim (1992) Methods in Enzymol. 216:362-368), and horseradish peroxidase. In a preferred embodiment, the indicator gene is green fluorescent protein (U.S. Pat. No. 5,491,084; WO96/23898).

The polynucleotides of the invention can be incorporated into pharmaceutical compositions suitable for administration. Such compositions typically comprise the nucleic acid molecule and a pharmaceutically acceptable carrier. As used herein the language "pharmaceutically acceptable carrier" is intended to include any and all solvents, dispersion media, coatings, antibacterial and antifungal agents, isotonic and absoftion delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration.

The invention is described below by way of the following examples which are to be construed as merely illustrative and not limitative of the scope of the invention.

EXAMPLES

Material and Methods

Cells and Reagents 293T cells (ATCC: CRL-11268) were maintained in Dulbecco's Modified Eagle's Medium (DMEM, Invitrogen) supplemented with 10% Fetal Bovine Serum (FBS, Invitrogen), 1% essential amino-acids and antibiotics. Human mesenchymal stem cells (hMSCs) were obtained from Inbiobank (www.inbiobank.org; San Sebastian, Spain), and were cultured in Advanced-DMEM (Gibco) plus 10% FBS. When cell cultures achieved over 85% of density, adherent cells were trypsinized, washed in PBS and re-plated at a concentration of $5 \times 10^3$ cells/$cm^2$.

Plasmids Construction

Dual System:

StetR and CTetOE. The StetR vector plasmid was obtained by replacing EGFP cDNA from the pHRSIN-CSEW (Demaison et al., Hum Gene Ther 2002; 13: 803-13) plasmid (using BamHI and NotI excision) with a TetR cDNA obtained by PCR using pcDNA6TR (Invitrogene) as a template and the BamH1-tetR Fw (5' GGATCCAT-GTCTAGATTAGATAAAAG, SEQ ID NO: 18) and Not-TetR reverse (5' GCGGCCGCTTAATAAGATCTGAATTC-CCGGG, SEQ ID NO:19). Primers to include the BamHI NotI sites at both ends. To construct the CTetOE vector plasmid, we used pHRSIN-CSEW vector as backbone, excising the SFFV promoter using EcoRI/BamHI restriction enzymes. A PCR fragment containing CMVTetO cassette was obtained by PCR using the EcoR1 forward (CCG GAATTCGTTGACATTGATTATTGACTA, SEQ ID NO:20) and BamH1 reverse (CGC GGATCCCGGAAGATGGATCGGTCC, SEQ ID NO:21) primers and the pcDNA4/TO plasmid (Invitrogene) as template.

All-in-One CEST Lentiviral Vector:

The CEST vector plasmid harboring the CMV-tetO regulatable cassette driving the expression of GFP as well as the spleen focus-forming virus promoter driving the expression of the TetR repressor gene was constructed by cloning the SFFV-TetR PstI fragment from the STetR vector into the unique PstI restriction site of the CTetOE vector.

Vector Production and Titration

The HIV packing plasmid (pCMVDR 8.9) and VSG-G plasmid (pMD.G) are described elsewhere (Naldini et al., 1996, Science 1996: 272:263-7 and Zufferey et al., 1998, J. Virol. 1998. 72: 9873-80). Vector production was performed as described previously (Toscano et al., 2004, Gene Ther 2004; 11: 956-61). Briefly, 293T cells, were plated, and the vector, packaging, and envelope plasmids (plasmid proportion 3:2:1) were resuspended in 1.5 ml of Opti-MEM (GIBCO) mixed with 60 µl of Lipofectamine 2000 (Invitrogen, Carlsbad, Calif.) and diluted in 1.5 ml of Opti-MEM (GIBCO). The mixture was added to the 293T cells, which were incubated for 6-8 h, washed and cultured for an additional 48 h. Viral supernants were collected and filtered through a 0.45 µm (pore size) filter (Nalgene, Rochester, N.Y.) aliquoted and immediately frozen at −80° C. For the titration of vectors, transduced cells were lysed and DNA extracted after 7-10 days, and vector copy number per genome (v.c.g) was determined using quantitative PCR as described below.

DNA Extraction and Quantitative Real-Time PCR

Genomic DNA was isolated by adding 1 ml per 106 cells of SNET extraction buffer (20 mM Tris-HCl [pH 8], 5 mM EDTA [pH 8], 400 mM NaCl, 1% SDS) containing proteinase K (100 mg=ml; Sigma-Aldrich). DNA samples were incubated at 55° C. for 2-18 hr, proteinase K was inactivated by incubating at 958 C for 10 min, and 30 RNase (1 mg=ml) was finally added for 30 min at 37° C. Proteins were extracted twice with phenol-chloroform, and DNA was then precipitated and its concentration determined by spectrophotometry. Quantitative real-time PCR were performed with an Mx3005P system (Agilent). The real time PCRs were performed using the QuantiTectO QUANTITECT® SYBR® Green PCR Kit (from Qiagen). To quantitate lentiviral integration we used primers for the WPRE sequence; WPRE-F: 5'-CACCACCTGTCAGCTCCTTT (SEQ ID NO: 22) and WPRE-R: 5'-ACAACACCACGGAATT-GTCA (SEQ ID NO: 23) The parameters for the PCR were 1× (95° C., 2 min); 40× (95° C., 15 sec/63° C., 30 sec/72° C., 30 sec); 1× (72° C. 2 min). We calculated the vector copy number per genome by interpolation in the standard curve made with 10-fold increasing amounts of plasmid DNA (CTetOW)) from $10^3$ to $10^7$ copies and by starting with 0.6 ug genomic DNA (about 100.000 genomes)

Cell Extraction and Western Blotting.

Cytosolic and nuclear fraction of transduced cells were obtained using the QPROTEOME® nuclear protein Kit (Qiagen) following manufacturer's instruction. Proteins were resolved by sodium dodecyl sulfate-polyacrylamide gel electrophoresis (SDS-PAGE; 10% polyacrylamide gels, reducing conditions), and electrotransferred to Hybond-P polyvinylidene difluoride (PVDF) membranes (GE Healthcare Life Sciences, Buckinghamshire, UK). Membranes were blocked with 5% nonfat milk and probed for 1 hr at room temperature with rabbit anti-GRB2 (BD pharmingen; no 559266), rabbit anti-actin (Sigma; A5060) and mouse anti-Tet-repressor (Mobitec; TET02). Combination of IRDYE® 680LT Goat anti-Rabbit IgG (Licors: 26-68021) and IRDYE® 800CW Goat anti-Mouse IgG (Licors: 926-32210) were use at 1:10.000 dilutions to analyzed TetR protein in combination with either actin or GRB2. After washing the membranes, detection and quantification of protein were performed using ODYSSEY® Image Scanner System (Licor Biosciences, Cambridge, UK) using IRDYE®-conjugated secondary antibodies (Licor) and the ODYSSEY® quantification software.

Immunostaining

For immunofluorescence analysis of cultured cells, cells were fixed in 4% paraformaldehyde-PBS for 20 min, permeabilized with 0.1-1% TRITON® X-100-PBS for 15 min, and blocked with 5% PBS for 45 min at room temperature (RT). Fixed cells were incubated with 2 ug/ml anti-Tet-repressor (Mobitec; TET02) and then with a secondary FITC-conjugated anti-mouse IgG (Becton Dickinson (BD)). Stained cells were then mounted in VECTASHIELD® mounting medium with DAPI (H-1500, vector laboratories) and examined using an Olympus AX60 fluorescence microscope.

Phenotype of hMSCs

MSCs were collected, washed and pre-incubated in a PBS-blocking solution containing 3% of fetal bovine serum (FBS) and 0.2% sodium azide for 15 minutes at 4° C. The following antibodies were used to fully characterize expression pattern of transduced and untransduced MSCs: anti human CD90-FITC, CD73-PE, CD105-FITC, CD166-PE, CD106-PE, CD45-PERCP, CD34-APC, HLA-DR-PERCP, CD19-APC all form Becton Dickinson (BD). Antibodies were diluted in PBS 0.3% of FBS and 0.02% sodium azide. Cells were incubated with 100 μl of the different antibodies (1/100), for 1 h at 4° C. and agitation and washed in PBS 0.3% of FBS and 0.02% sodium azide followed by a final wash in PBS alone. Cells were analyzed in FACScan Flow Cytometer.

Fold Induction Index and Leakiness Determination.

Transduced cells incubated in the presence or absence of different concentrations of doxycycline were analyzed by flow cytometry to determine the percentage of eGFP positive cells and the Mean fluorescence intensity (MFI) of either, the eGFP+ population or the entire population.

The Fold induction index was estimated as arbitrary units obtained by following formula:

[% eGFP+(+Dox)/% eGFP+(−Dox)]×[MFI eGFP+ cells(+Dox)/MFI eGFP+cells(−Dox)]

Leakiness of the system was determined by using the following formula:

[% eGFP+(−Dox)/% eGFP+(+Dox)]×MFI eGFP+ cells(−Dox)

Cell Cycle Analysis.

Cell Cycle assays were performed as previously described [21]. Briefly, the trypsinized cells were fixed in 70% ethanol, washed with PBS, and then incubated with Propidium Iodide (20 mg/ml) in PBS containing RNase A for 30 min at 37° C. After washing, cells were analyzed by flow cytometry (FACScan, Becton Dickenson).

Example 1

The Binary Lentiviral Vector System Based on Original TetR Repressor Achieves High Induction and Low Background in Bulk Populations Based on the two key expression vectors of the T-REX™ Expression System (pcDNA4/TO-E and pcDNA/TR, Invitrogen), an alternative two lentiviral vector system based on pHRSIN-WPRE lentiviral vector was constructed (FIG. 1A). The first vector expresses the TetR repressor (STetR) through the SFFV promoter and the second expresses eGFP through the regulatable CMV-TetO promoter (CTetOE) (see M&M). The titre obtained with the StetR vector was above 10.000.000 tu/ml before concentration. The high titre together with the wide tropism of the SFFV promoter allowed the easy generation of stable bulk cell lines expressing high level of the TetR repressor. Using this system we developed 293T cell lines highly responsive to low concentration of doxycycline (FIG. 1B).

Example 2

Figure 2:
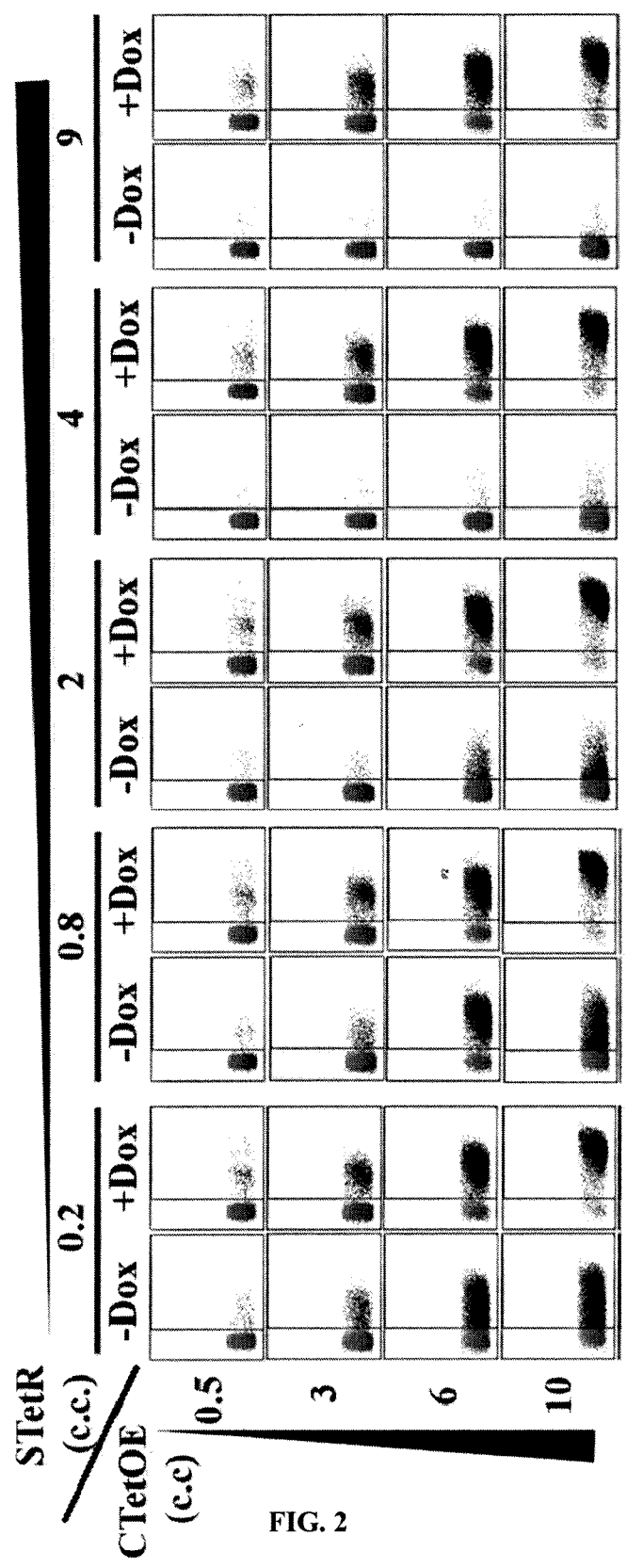
FIG. 2 GFP induction level using binary lentiviral vectors. A) 293T cells were stably transduced with increasing amount of STetR lentiviral vector. Different TetR-expressing 293T cell lines were generated each harbouring an average of 0.2, 0.8, 2, 4 and 9 copies per cell (c.c.) (indicated on the top of Figure A). Each of these TetR-expressing 293T cell lines where later transduced with increasing amount of CTetOE vectors (average of 0.5, 3, 6 and 10 c.c) (indicated on the left of figure A). Plots show eGFP expression of the different cell lines in the absence (−Dox) or presence (+Dox) of 1 µg of doxycycline. B. Graph showing the increment in fold induction of transduced 293T cells after the addition of 100 ng/ml of doxycycline. The highest induction levels are achieved when the cells contain multiple copies of both StetR (7-9 copies) and CTetOE vectors (6-10 copies).
Figure 2:
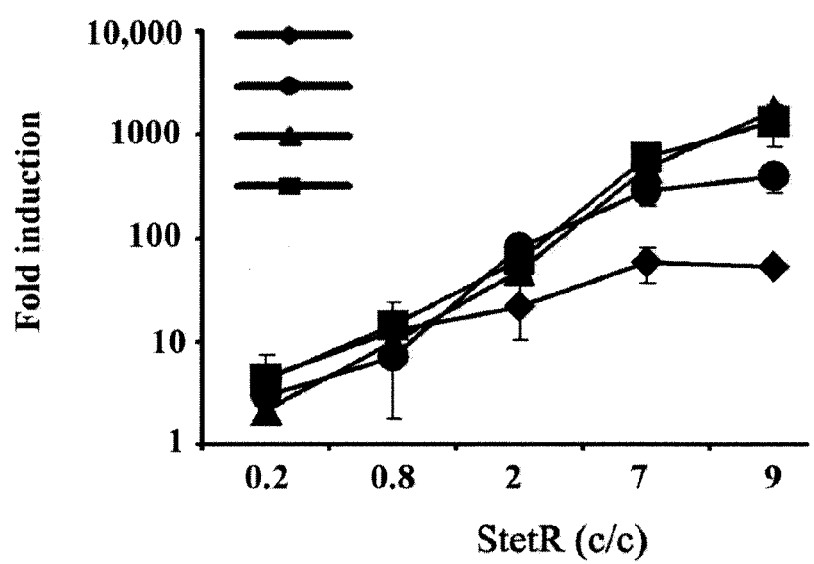

High Induction and Low Leakiness of the TetR-Based System is Dependent on High TetR Concentration but Independent on CMVTetO Target Sites Transactivator-containing repressor (tTA and rtTA) are quite toxic for most of the cells and must be kept at low concentration. In order to achieve good regulation, the concentration of TetO binding sites must be kept low to equal low repressor concentrations. It was therefore studied whether this was also the case for the unmodified TetR-based systems by using STetR and CTetOE lentiviral vectors. Increasing amounts of STetR were used to obtain 293T cell lines with increasing amounts of TetR repressor (FIG. 2A; from left to right). All these 293T-TetR cell lines were transduced with increasing amounts of the CTetOE to obtain increasing concentrations of CMVTetO targets (FIG. 2A: from top to bottom). It was shown that only those cells expressing high levels of TetR repressor have good induction and low leakiness (FIG. 2A right panels). A minimum of 2 copies of the STetR vector is required in order to achieve good regulation and over 3-4 copies gives minimal background and maximal induction (FIG. 2A; second right graphs). Interestingly, there was a direct correlation between the CTetO vector copies per cell (c.c) and the fold induction index (FIGS. 2A and 2B). Over 1000 fold induction was reached in bulk populations containing around 7 c.c of the STetR vector and 6 c.c of the CTetoE vector. (FIG. 2B). This indicates that the TetR repressor, contrary to the rtTA transactivator, can be express in excess to be able to bind and modulate a high number of TetO operons.

Example 3

Figure 3A:
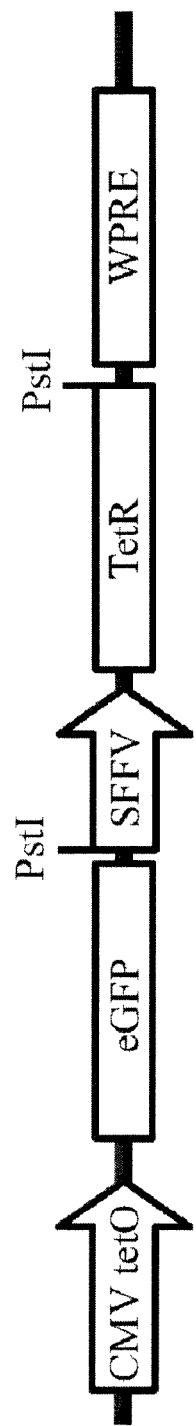
FIG. 3. Easy generation of highly responsive cell lines with the all-in-one doxycline-controllable lentiviral vector CEST. A). Schematic representation of the CEST. eGFP transgene is expressed from a Tetracycline-responsive CMV-TetO promoter and the TetR repressor is expressed from the SFFV promoter. B) Doxycycline responsiveness of 293T containing different amounts of CEST vector copy per cell (0 (Mock), 0.4, 4 and 20 c.c as indicated on the left hand side). The different cell lines were incubated in the absence of doxycycline (−Dox), and with 0.001 µg/ml, 0.01 µg/ml and 0.1 µg/ml as indicated on the top. The leaking in the absence of doxycycline decrease as the vector copy number increase (left graphs from top to bottom). C) Fold induction (left panels) and leaking (right panels) in 293T (top panels) and human mesenchymal stem cells (hMSC) (bottom panels) transduced with increasing MOIs of the CEST vector. The average CEST vector copies per genome of the different cell lines analyzed are indicated at the bottom of the graphs. The best regulation in terms of higher inducibility and lower leaking is achieved in the cells that contain the highest number of CEST vector integrated.
Figure 3B:
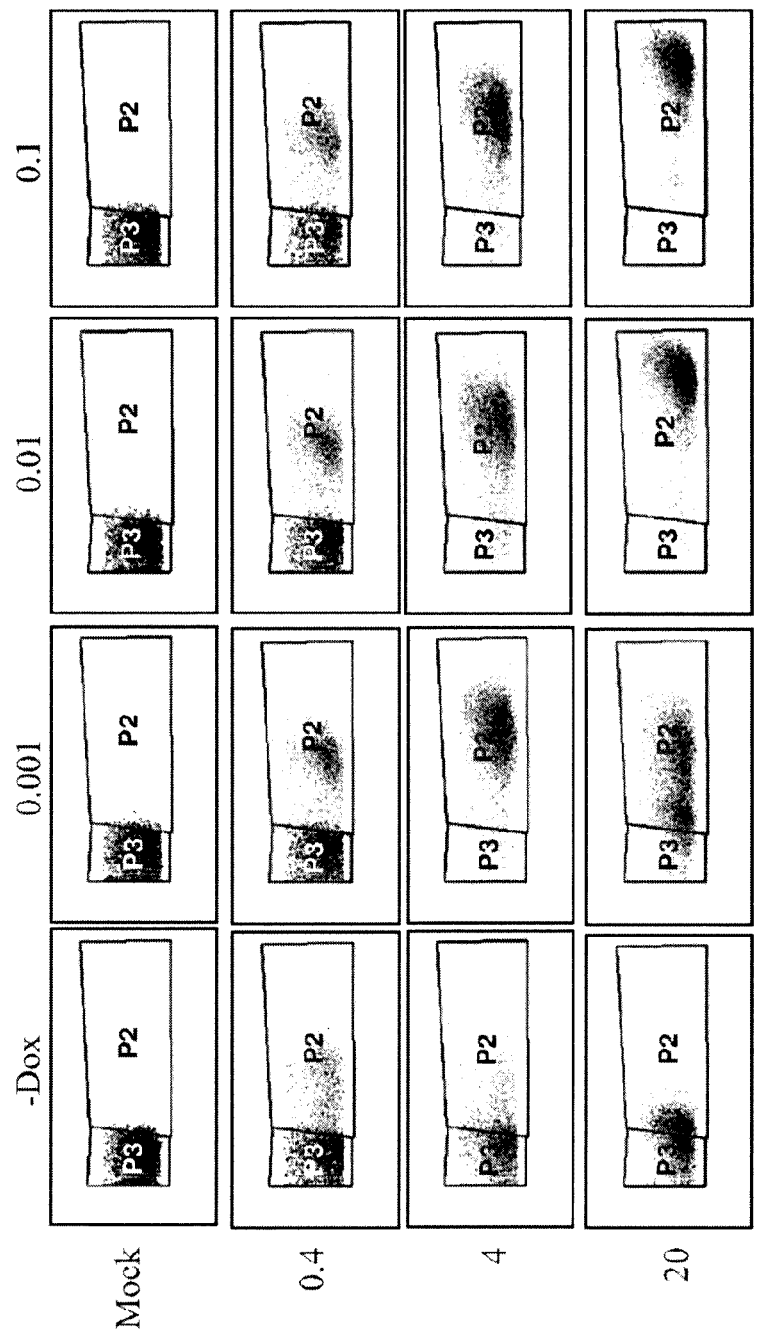
Figure 3C:
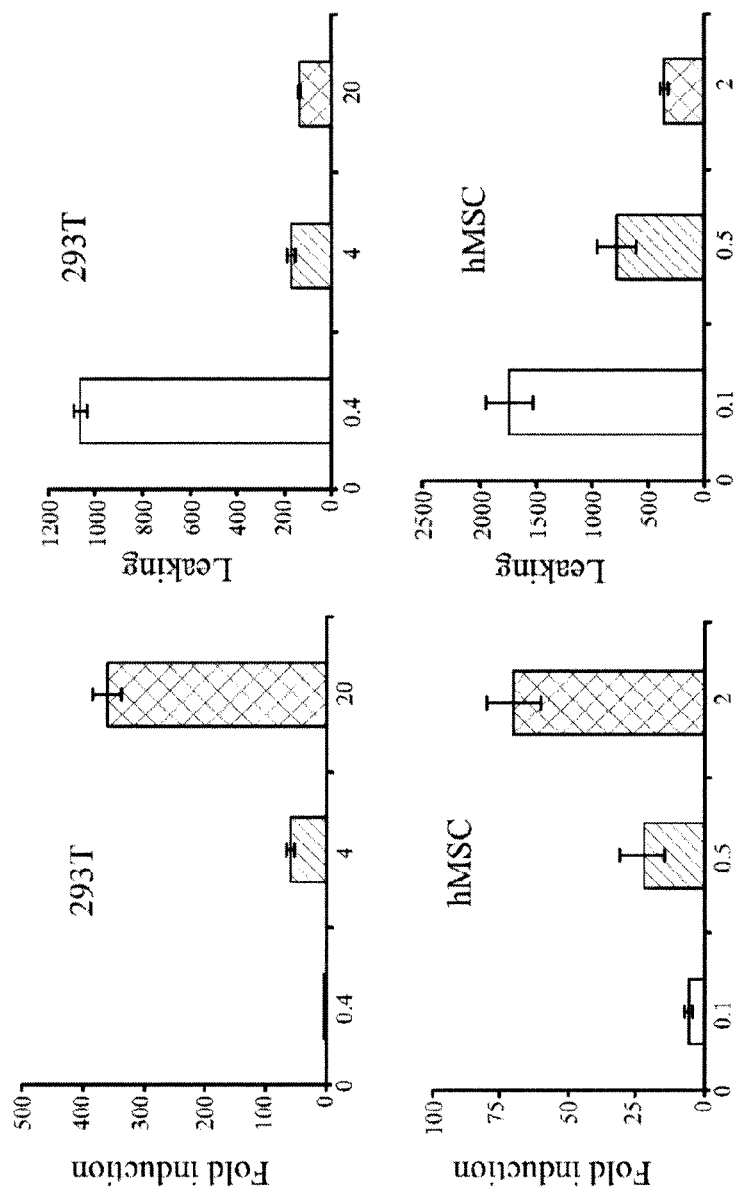

Development of all-in-One LV that Efficiently Regulates Transgene Expression in a Dose Dependent Fashion Although a two vector system has several applications in basic research, the generation of a single vector able to deliver the TetR repressor and a CMVTetO expression cassette is required for easy generation of Doxycycline-responsive primary cell lines and for gene therapy strategies. Therefore, a bicistronic lentiviral vector was constructed containing both, the doxycycline-responsive cassette (CMVTetO) and the TetR expressing cassette (SFFV-TetR) (FIG. 3a). The all-in-one vector was tested in immortalized (293T) and primary (MSCs) cells. Interestingly, as for the two-vector system, the single vector requires also several copies to achieve good regulation (FIGS. 3b and 3c). In fact, not only the fold induction was higher at higher MOI in both cell lines (FIGS. 3b and 3c; left graphs) but there was also less leaking (FIGS. 3b and 3c; right graphs). These data corroborate the hypothesis of the requirement of high TetR concentrations as the main factor to achieve good regulation. Indeed, in this system, cells containing multiple copies of STetR will contain the same number of TetO targets and still, the leakiness drop with increasing MOIs.

Figure 4:
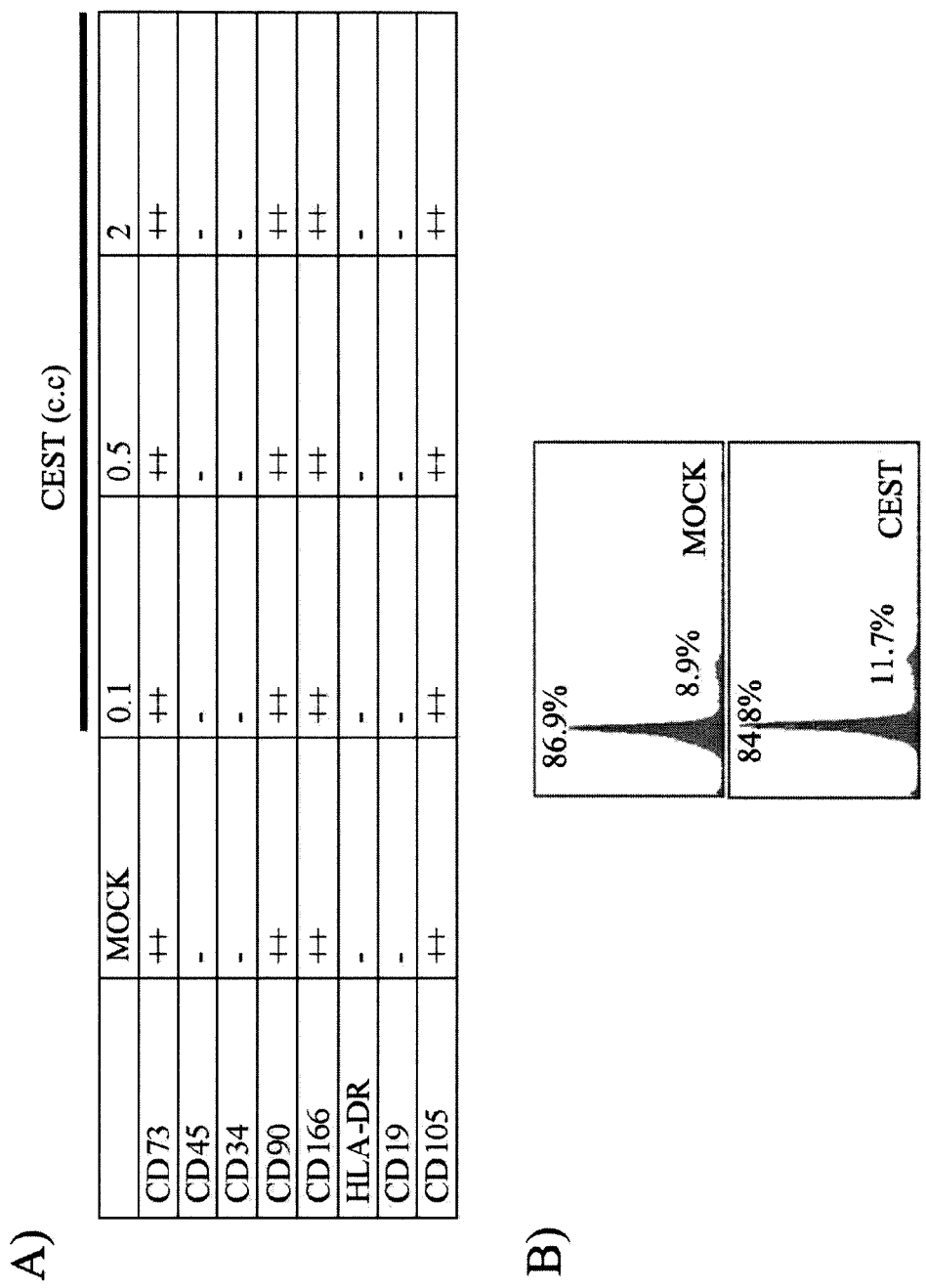
FIG. 4. Doxycycline-responsive human mesenchymal stem cells (hMSCs) maintain the main properties of parental hMSCs. A) Different doxycycline-responsive hMSCs were generated with increasing MOIs of the CEST vector to obtain an average of 0.1, 0.5, and 2 c.c. (indicated on the top of figure A) Expression of the different surface markers were analyzed by flow cytometry and compared to the expression by a parental (MOCK-transduced) hMSCs. B) The hMSCs containing 2 c.c. of the CEST vector was further analyzed to test the influence of vector expression on cell cycle status. No significant differences were observed between the parental and the CEST-transduced hMSCs.

MSCs are an important target for cell-gene therapy applications. Their role in regeneration, immunomodulation as well as their migratory capabilities to inflammatory locations makes them an attractive target for gene manipulation. The development of an efficient doxycycline-responsive gene transfer system to achieve high levels of transgene expression in MSCs (without affecting its phenotype) is of special interest for the field. Thus, the potential changes on doxycycline-responsive hMSCs compared with parental hMSCs were studied. No changes on either the expression of the main surface markers (FIG. 4A) nor in the cell cycle status (FIG. 4B) could be detected.

Example 4

Development of an Improved LV that Efficiently Regulates Transgene Expression in a Embryonic Stem Cells The CEST vector is very efficient modulating transgene expression in immortalized cell lines and in highly permissive primary cells such as mesenchymal stem cells. However, in cells that are difficult to transduce, such as the human embryonic stem cells (hESCs), the vector is not able to block expression and has a strong leaking. The reason for this is the requirement of integrate 2-4 copies of CEST per cell in order to achieve the TetR concentrations necessary to stop gene expression. The CEST vector was improved by:
a—Increasing the nuclear translocation of the TetR repressor. This was achieved by including a nuclear localization signal at the N-terminus: TetRn.
b—Expressing the TetRn through stronger promoters. This was achieved by using the Ef1alpha promoter.

Figure 5:
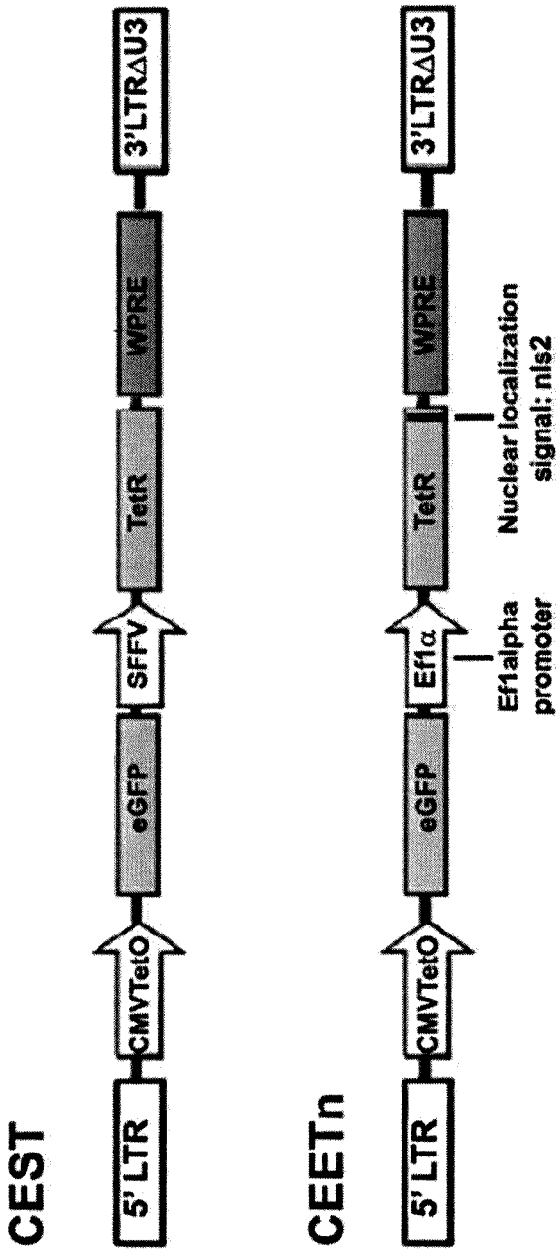
FIG. 5. Development of the CEETn. The CEETn (bottom) was constructed using the CEST vector (top) as backbone. We made two modifications: 1—Inclusion of a nuclear localization signal to the TetR (NLS2) and 2—Changing the SFFV promoter for the Ef1alpha promoter.

An schematic drawing of this new vector in comparison to the CEST vector is shown in FIG. 5.

Figure 6A:
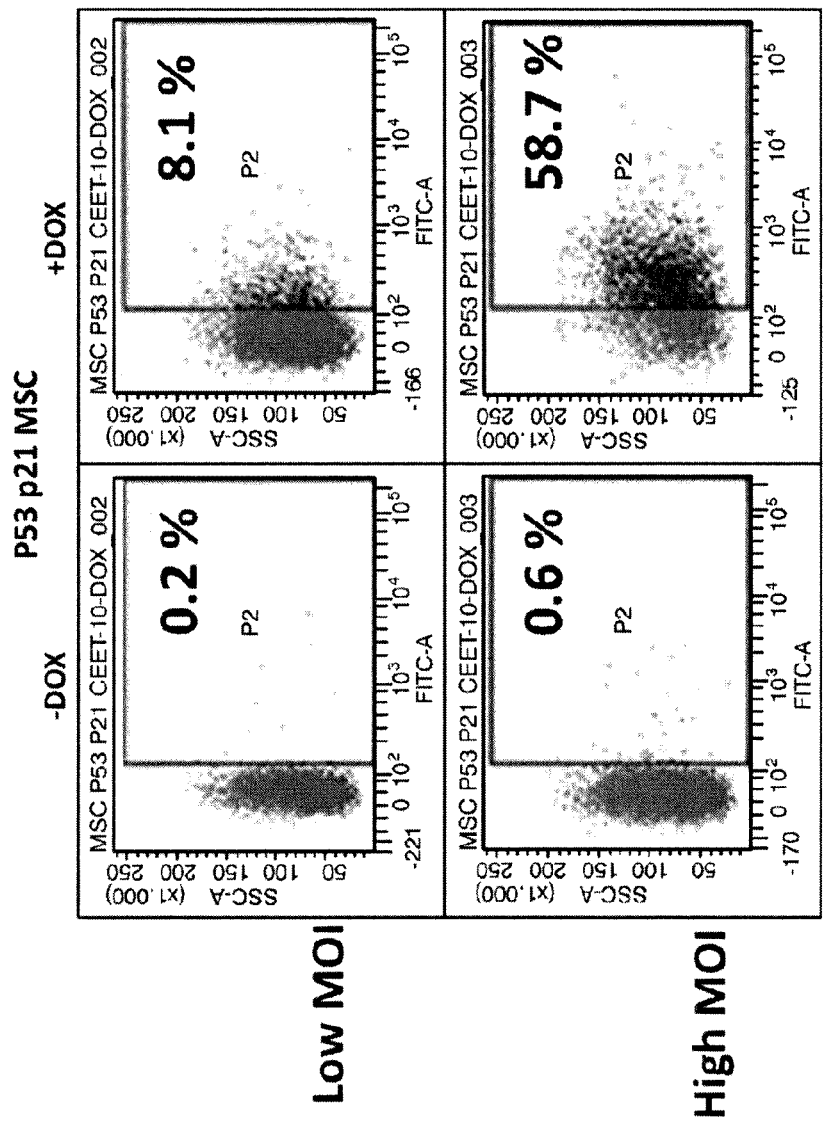
FIGS. 6A-6C. The CEETn efficiently modulate transgene expression at low copy number. Otice the low leaking (no transgene expression in absence of doxycicline) and good inducibility after doxycicline addition in mouse (left panels) and human (middle pplots) mesenchymal stem cells (MSC) as well as in 293T cells.
Figure 6B:
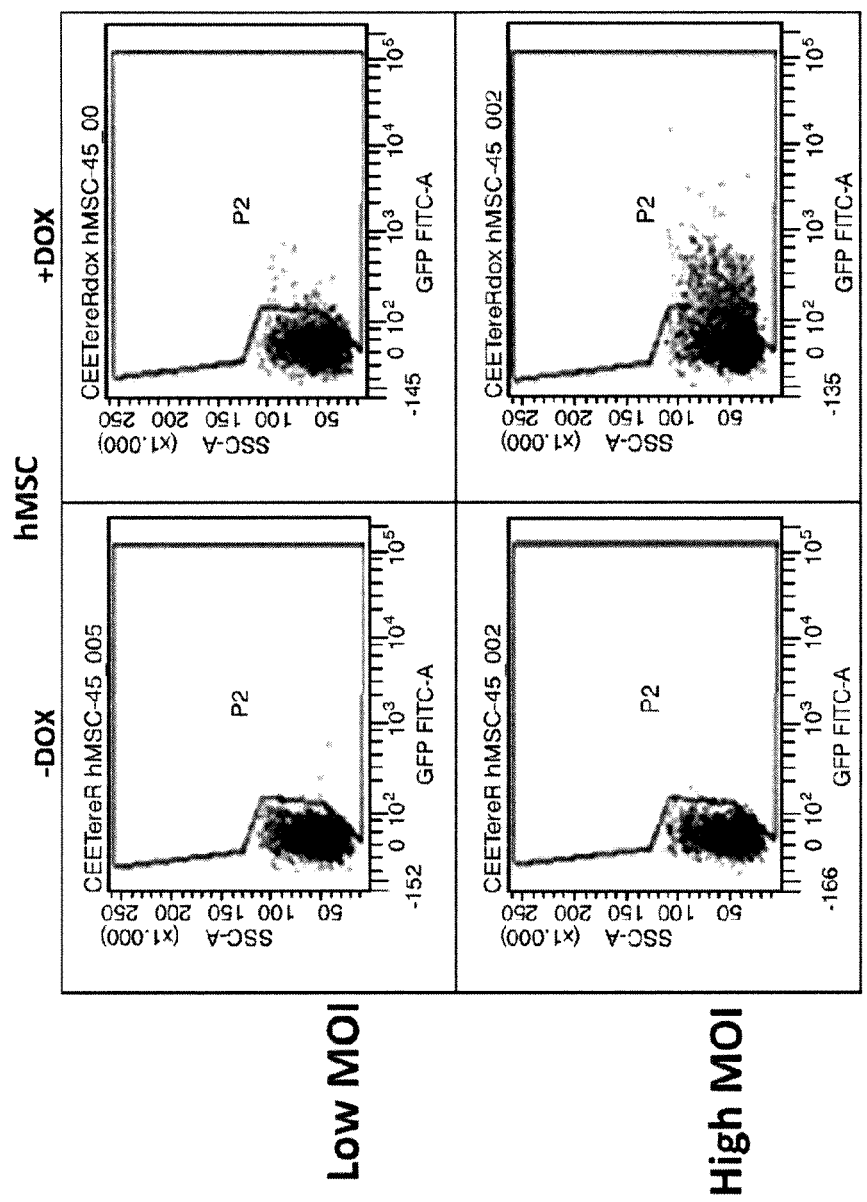
Figure 6C:
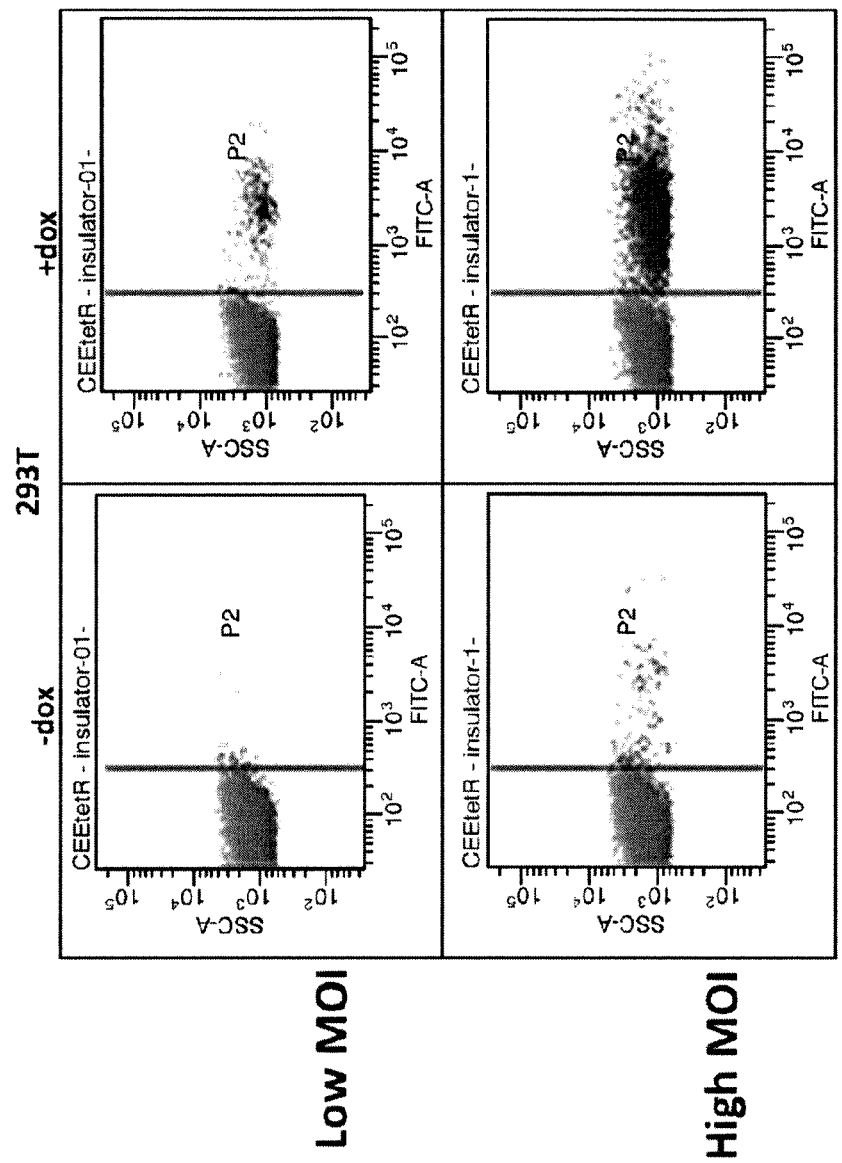

This vector (hereinafter referred to as CEETn all-in-one) is very efficient modulating transgene expression in most cell lines analyzed even at low copy number per cell (see FIG. 6).

Figure 7A:
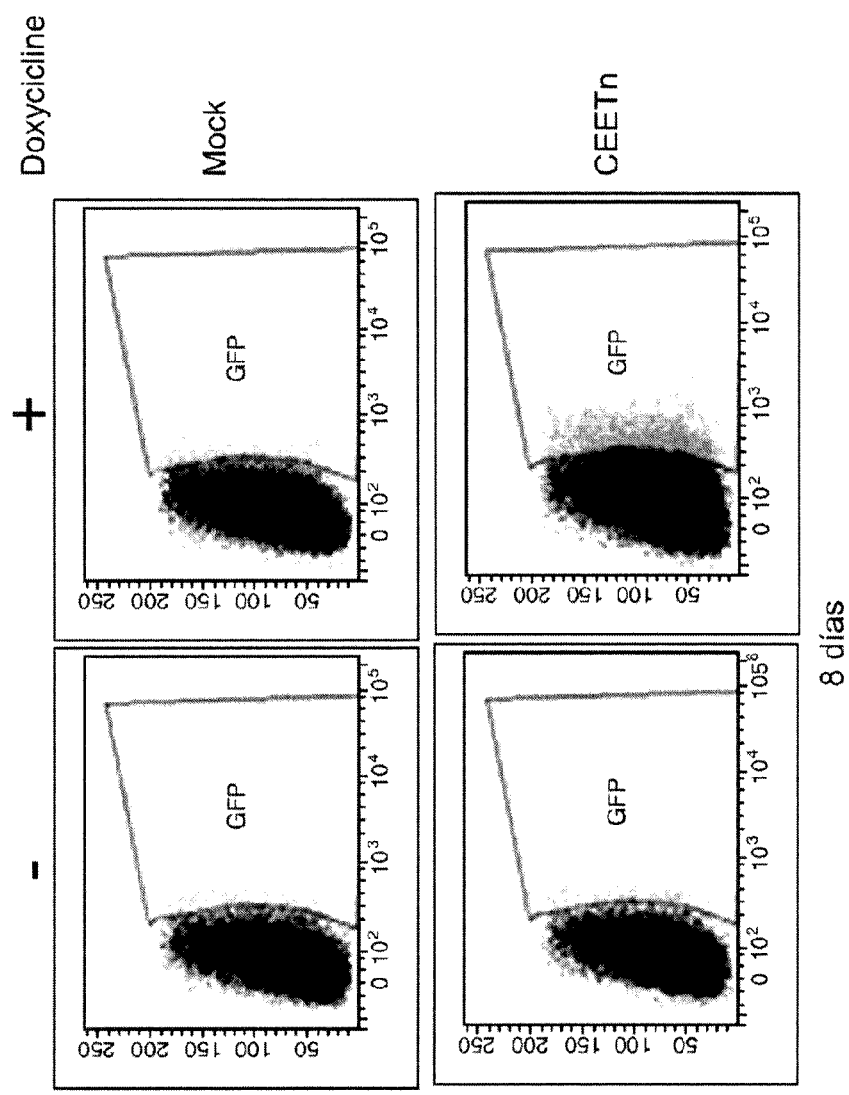
FIGS. 7A-7C. The CEETn lentiviral vector modulate transgene expression in bulk populations of human embryonic stem cells (hESCs). A) Dot plots showing eGFP expression of untransduced (Mock) and CEETn-transduced hESCs (CEETn) with (+) and without (−) doxycicline 8, 22 and 50 days after transduction.
Figure 7B:
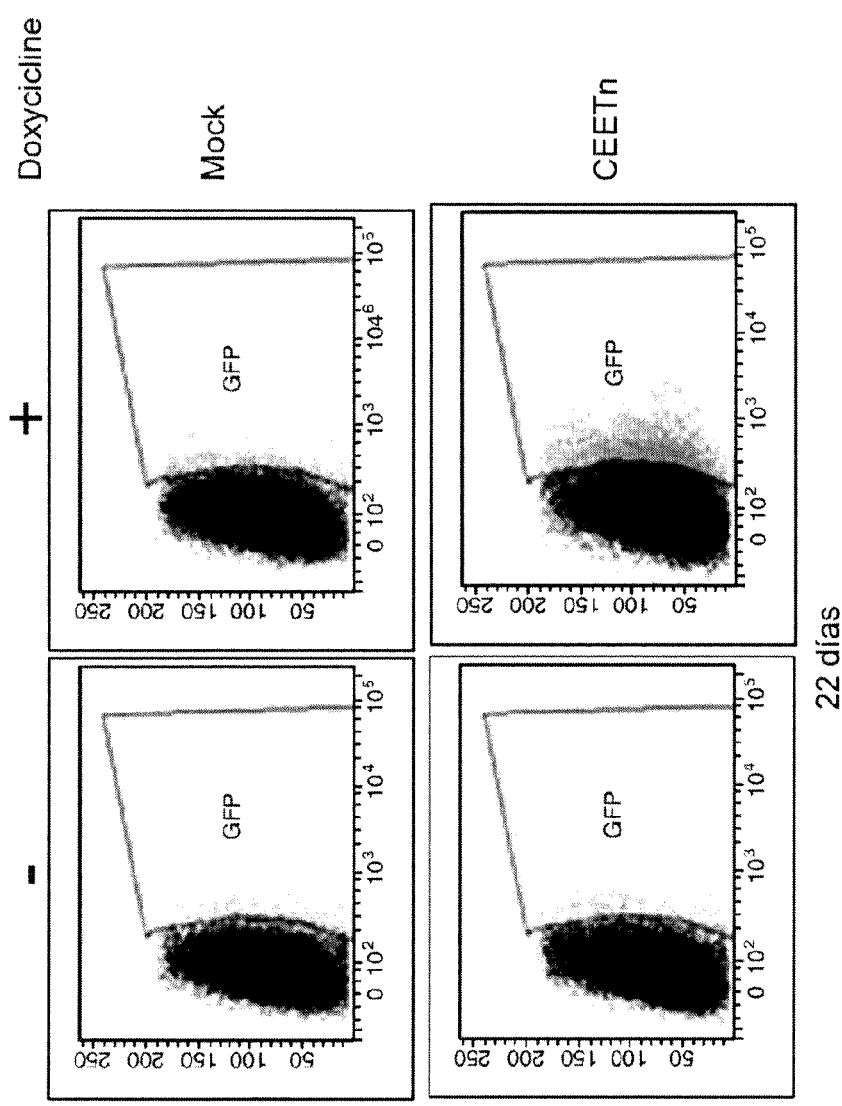
Figure 7C:
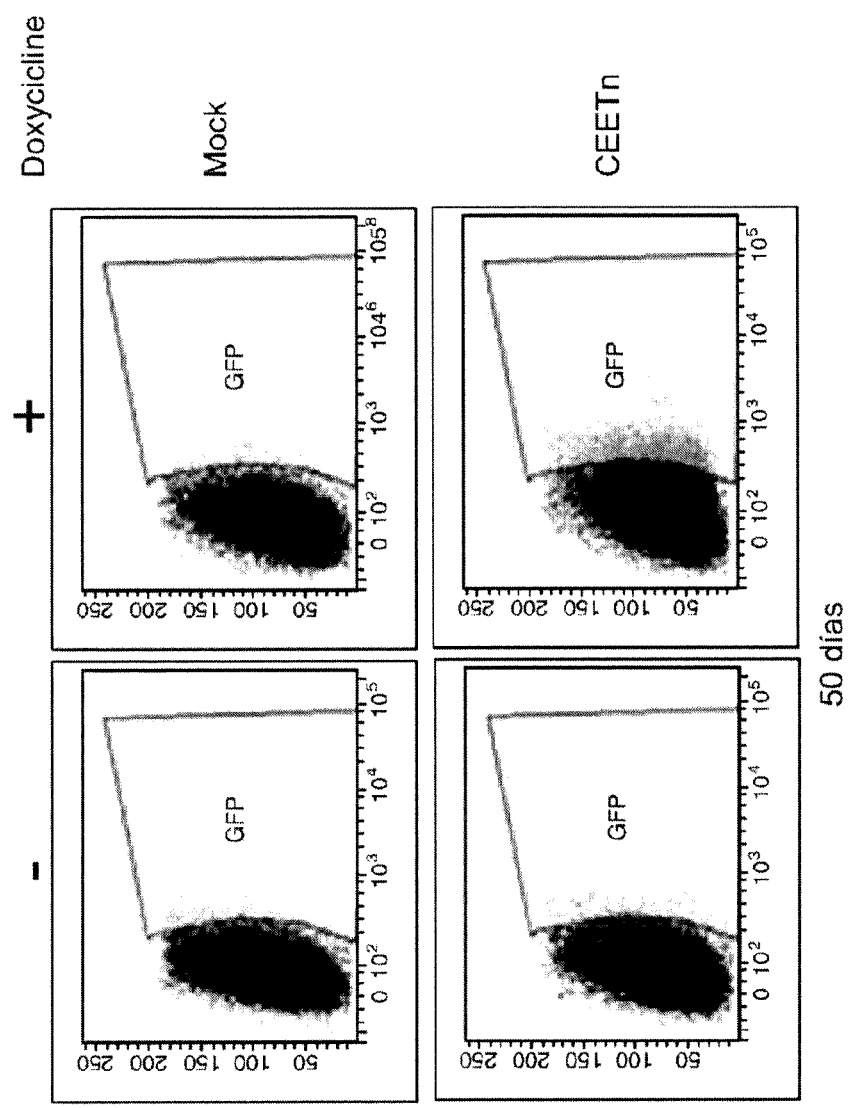

Importantly, the CEETn vector modulate transgene expression in human embryonic stem cells without the requirement of sorting and/or antibiotic selection. (see FIG. 7) This is, to our knowledge, the first all-in-one vector able to modulate transgene expression in embryonic stem cells.

The invention claimed is:

1. A polynucleotide comprising
   (i) a transcriptional regulatory sequence comprising a first promoter and at least one binding site for a transcriptional repressor wherein said first promoter and said binding site for a transcriptional repressor are arranged so that the binding of the transcriptional repressor to said binding site inhibits the transcriptional activity of the promoter and
   (ii) an expression cassette comprising a polynucleotide encoding a regulatable transcriptional repressor under the operative control of a second promoter wherein said regulatable transcriptional repressor is capable of specifically binding to the binding site in the transcriptional regulatory sequence in the absence but not in the presence of a ligand thereof,
   wherein the first promoter is the cytomegalovirus (CMV) immediate early promoter, wherein the second promoter is the spleen focus forming virus long terminal repeat (SFFV LTR) promoter; and
   wherein the transcriptional activity of the first promoter differs by less than 10% from the transcriptional activity of said first promoter when the transcriptional regulatory sequence (i) and the expression cassette (ii) are found in separate vectors.

2. The polynucleotide according to claim 1 wherein the binding site for a transcriptional repressor comprises at least a TetO operator sequence and wherein the regulatable transcriptional repressor is the tetracycline repressor.

3. The polynucleotide according to claim 1 wherein the binding site for the transcriptional repressor is downstream of the first promoter.

4. The polynucleotide according to claim 1, wherein the regulatable transcriptional repressor further comprises a nuclear localization signal.

5. The polynucleotide according to claim 1 further comprising a polynucleotide of interest under operative control of the transcriptional regulatory sequence.

6. An expression vector comprising the polynucleotide according to claim 1.

7. A lentiviral particle comprising the vector according to claim 6.

8. A host cell comprising the vector according to claim 6.

9. A composition or kit-of-parts comprising
(i) a first polynucleotide comprising transcriptional regulatory sequence comprising a first promoter and at least one binding site for a transcriptional repressor wherein said first promoter and said binding site are arranged so that the binding of the transcriptional repressor to said binding site inhibits the transcriptional activity of the promoter, and
(ii) a second polynucleotide comprising an expression cassette comprising a polynucleotide encoding a regulatable transcriptional repressor under the operative control of a second promoter wherein said regulatable transcriptional repressor is capable of specifically binding to the binding site in the transcriptional regulatory sequence in the absence but not in the presence of a ligand thereof, wherein the first promoter is the cytomegalovirus (CMV) immediate early promoter,
wherein the second promoter is the spleen focus forming virus long terminal repeat (SFFV LTR) promoter; and
wherein the first promoter differs by less than 10% from the transcriptional activity of said first promoter when the transcriptional regulatory sequence (i) and the expression cassette (ii) are found in separate vectors.

10. A composition or kit-of-parts according to claim 9 wherein the binding site for a transcriptional repressor is a binding site for the tetracycline repressor and wherein the regulatable transcriptional repressor is the tetracycline repressor.

11. A composition or kit-of-parts according to claim 10 wherein the binding site for the tetracycline repressor is a TetO operator sequence.

12. A composition or kit-of-parts according to claim 9 further comprising a ligand of the transcriptional repressor which, when bound to the repressor, results in the inactive repressor which is no longer capable of binding to its binding site in the transcriptional regulatory sequence.

13. A method for regulating the expression of a nucleic acid sequence of interest comprising the steps of
(i) providing a host cell comprising the polynucleotide according to claim 1 wherein the nucleic acid of interest is operatively linked to the first promoter in said polynucleotide, and
(ii) contacting said host cell which with a ligand for the transcriptional repressor wherein said ligand is capable of binding to the transcriptional repressor producing an inactive repressor which is released from its binding site in the transcriptional regulatory sequence thereby allowing the transcription of the nucleic acid driven by the first promoter.

14. A method for regulating the expression of a nucleic acid sequence of interest comprising the steps of
(i) providing a host cell comprising the first and second polynucleotides of the composition or kit-of-parts according to claim 9 wherein the nucleic acid is operatively linked to the first promoter of the first polynucleotide, and
(ii) contacting said host cell which with a ligand for the transcriptional repressor wherein said ligand is capable of binding to the transcriptional repressor producing an inactive repressor which is released from its binding site in the transcriptional regulatory sequence thereby allowing the transcription of the nucleic acid driven by the first promoter.

\* \* \* \* \*